US005677350A

United States Patent [19]

Frydman

[11] Patent Number: 5,677,350
[45] Date of Patent: Oct. 14, 1997

[54] INHIBITION OF CANCER CELL GROWTH, PROLIFERATION, AND METASTASIS USING N,N'-DIBENZYL-α,ω-DIAMINOALKANES

[75] Inventor: Benjamin J. Frydman, Madison, Wis.

[73] Assignee: Wisconsin Alumni Research Foundation, Madison, Wis.

[21] Appl. No.: 472,431

[22] Filed: Jun. 7, 1995

[51] Int. Cl.$^6$ .................. A61K 31/13; A61K 31/135
[52] U.S. Cl. .................................................. 514/655
[58] Field of Search .................................... 514/655

[56] References Cited

U.S. PATENT DOCUMENTS

| | | | |
|---|---|---|---|
| 4,330,559 | 5/1982 | Bey et al. | 424/319 |
| 4,413,141 | 11/1983 | Bey et al. | 562/561 |
| 4,499,072 | 2/1985 | Sunkara et al. | 424/85 |
| 4,902,719 | 2/1990 | Gerhart et al. | 514/564 |
| 4,914,240 | 4/1990 | Gerhart et al. | 564/478 |
| 4,925,835 | 5/1990 | Heston | 514/183 |
| 4,935,449 | 6/1990 | Bey et al. | 514/671 |
| 5,002,870 | 3/1991 | Bowlin et al. | 435/71.1 |
| 5,344,846 | 9/1994 | Jakus et al. | 514/634 |

OTHER PUBLICATIONS

Bolkenius, Frank N., and Seiler, Nikolaus, New Substrates of Polyamine Oxidase, Dealkylation of N–Alkyl–α–ω–Diamines, *Biol. Chem. Hoppe–Seyler* (1989), 370:525–531.

Jakus, Judit; Wolff, Edith C.; Park, Myung Hee; and Folk, J.E., Features of the Spermidine–binding Site of Deoxyhypusine Synthase as Derived from Inhibition Studies, *The Journal of Biological Chemistry* (1993), vol. 268, No. 18, pp. 13151–13159.

*Primary Examiner*—Jerome D. Goldberg
*Attorney, Agent, or Firm*—DeWitt Ross & Stevens SC

[57] ABSTRACT

The present invention relates to the inhibition of cancer cell growth, proliferation, and metastasis by contacting cells with an N,N'-dibenzyl α,ω-diaminoalkane, a derivative of naturally-occurring putrescine. More specifically, the present invention relates to the treatment of cancer in humans by administration of a cancer cell growth-inhibiting amount of an N,N'-dibenzyl α,ω-diaminoalkane to a human cancer patient.

18 Claims, 25 Drawing Sheets

INHIBITION OF CANCER CELL GROWTH, PROLIFERATION, AND METASTASIS USING N,N'-DIBENZYL-α,ω-DIAMINOALKANES

FIELD OF THE INVENTION

The present invention relates to the inhibition of cancer cell growth, proliferation, and metastasis by contacting cells with an N,N'-dibenzyl-α,ω-diaminoalkane. More specifically, the present invention relates to the treatment of cancer in humans by administration of a cancer cell growth-inhibiting amount of an N,N'-dibenzyl-α,ω-diaminoalkane to a human cancer patient.

DESCRIPTION OF THE PRIOR ART

The polyamines spermidine, $H_2N(CH_2)_4NH(CH_2)_3NH_2$, and spermine, $H_2N(CH_2)_3NH(CH_2)_4NH(CH_2)_3NH_2$, and their mutual metabolic precursor, putrescine (or 1,4 butanediamine, $H_2N(CH_2)_4NH_2$), are present to some degree in all cells, and ubiquitous in proliferating cells. These polyamines are essential for both normal and neoplastic tissue growth.

Spermine and spermidine derive their characteristic common names due to their initial isolation from human semen. In fact, spermine was first observed in human semen and described as the crystalline phosphate salt by Anton Van Leeuwenhoek in 1678. (*Phil. Trans. Roy. Soc. London* 12, 1040). No less notably, putrescine, and its five-carbon analog, cadaverine (1,5-pentanediamine), derive their morbid-sounding common names from the fact that these diamines were first isolated from rotting corpses.

In vivo, the first step in the biosynthesis of spermidine and spermine is decarboxylation of ornithine (2,5-diaminopentanoic acid, $H_2N(CH_2)_3CH(NH_2)CO_2H$) by ornithine decarboxylase (ODC) to yield putrescine. Spermidine is then synthesized by transfer of an activated aminopropyl group from S-adenosyl S-methyl homocystaeamine to putrescine. Spermine is formed by addition of a further aminopropyl group to spermidine.

As noted above, these polyamines, which are ubiquitous in animal tissues and microorganisms, are known to play an important role in cell growth and proliferation. Induction of cell growth and proliferation is associated with a marked increase in ODC activity and a concomitant increase in cellular levels of putrescine, spermidine, and spermine. Although the exact mechanism of the role of the polyamines in cell growth and proliferation remains unclear, it appears that the polyamines may facilitate macromolecular processes such as DNA, RNA, or protein synthesis. Polyamines are known to bind to DNA, as well as to ribosomes. They also interact extensively with tRNA. Additionally, polyamines levels are known to be high in the testes, prostate, and thymus; in psoriatic skin lesions; and in other cells undergoing rapid growth processes.

Although polyamines are present to some degree in all cells, it is also known that rapid proliferation of tumor tissues is marked by an abnormal elevation of polyamine levels. The knowledge of elevated polyamine levels in a wide variety of rapidly proliferating cells has led many researchers to believe that polyamines are an important regulator of tumor growth. This, in turn, has led many researchers to investigate different reagents for ODC inhibitory effects, in the belief that by inhibiting ODC activity, and thereby blocking the formation of the polyamines, the growth and proliferation of transformed cells can be slowed, interrupted, or arrested entirely.

To date, the most successful ODC inhibitors have been α-functionalized methylornithine substrate analogs. (See, for instance, McCann et al., Pharmacol. Ther. 1992, 54:195–215). A very promising early ODC inhibitor, developed by Marion Merrell Dow, is difluoromethylornithine (DFMO), an irreversible inhibitor of ODC. DFMO and its use in the treatment of benign prostatic hypertrophy are described in two patents to Bey et al., U.S. Pat. Nos. 4,413,141, and 4,330,559, respectively.

Bey et al. '141 describe DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. In an interesting aside, DFMO is also an effective antiprotozoal agent for treatment against African trypanosomes (*Trypanosoma b. brucei, b. rhodesiense*, and *b. gambiense*), agents causative of African sleeping sickness.

Bey et al. '559 describe the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

The initial promise of DFMO as a therapeutic ODC inhibitor for use in the treatment of various neoplasias has dimmed somewhat because that, although DFMO does, in fact, irreversibly inhibit ODC activity (and is therefore sometimes described as a "suicide" inhibitor), cells treated in vivo with DFMO significantly increase their uptake of exogenous putrescine. (See, for instance, Heston, U.S. Pat. No. 4,925,835, described more fully, below.) In effect, the intercellular transport mechanisms of the cell do an "end run" around the DFMO-impaired ODC activity by importing putrescine from the extra-cellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in a host of common foods, such as orange juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Another drawback to DFMO and its derivatives is that although small molecules, they are relatively expensive to synthesize. The need for fluorination of a starting material or intermediate requires increased safety precautions and equipment which makes DFMO compounds difficult to synthesize at low cost.

However, because DFMO is an effective inhibitor of ODC, some researchers are attempting to use DFMO as part of a conjunctive treatment in combination with other therapeutic agents. For instance, Sunkara et al., U.S. Pat. No. 4,499,072, describe improving the polyamine-depletion effects of ODC inhibitors (including DFMO) by using interferon in combination with the ODC inhibitor. Additionally, Sunkara et al. describe the use of both an ODC inhibitor and interferon in conjunction with a known cytotoxic agent such as methotrexate.

Bowlin et al., U.S. Pat. No. 5,002,879, describe a similar conjunctive therapy in which an ODC inhibitor, preferably DFMO, is used in combination with lymphokine-activated killer (LAK) cells and interleukin-2. Both the Bowlin et al. patent and the Sunkara et al. patent are assigned to Merrell Dow Pharmaceuticals (a predecessor company of Marion Merrell Dow).

In addition to investigating inhibition of polyamine synthesis using substrate analogs, Heston, U.S. Pat. No. 4,925,835, describes the use of aziridinyl putrescine derivatives (product analogs) as cytotoxic agents for the treatment of prostate cancer. Heston notes that treatment with DFMO causes increased uptake of both putrescine and cadaverine by prostate tumor-derived cells. Heston uses the evidence of the increased uptake of extra-cellular putrescine and cadaverine upon exposure to DFMO to propose linking DFMO exposure with exposure to a cytotoxic putrescine derivative, namely 1-(4-aminobutyl) aziridine. Presumably, the increased uptake of putrescine caused by DFMO exposure will cause the cancer cells to import lethal (or cell growth-inhibiting) quantities of the aziridinyl putrescine analogs.

U.S. Pat. No. 4,902,719, to Gerhart et al., describes 5-position substituted ornithine derivatives which find use as L-ornithine:2-oxoacid aminotransferase (OAT) inhibitors, a mitochodrial enzyme found in many tissues, including liver, kidney, and brain. Like ODC, OAT acts upon ornithine. OAT catalyzed the transamination of L-ornithine to 2-oxoglutarate, with the simultaneous production of γ-semialdehyde and glutamate. In normal subjects, inhibition of OAT can lead to excess levels of ornithine. As a consequence, the OAT inhibitors described in this reference are used to treat subjects having low ornithine levels.

Another patent reference to Gerhart et al., U.S. Pat. No. 4,914,240, describes gem-dihalo-1,8-diamino-4-aza-octane derivatives which have anti-tumor and anti-proliferative effects. These compounds are gem-dihalo derivatives of spermidine in which two geminal halogens are located on either the 2 or 3 carbon of the aminobutyl portion of the molecule, or on the 2 carbon of the aminopropyl moiety. (See Gerhart et al., column 1, line 60.) Here, Gerhart et al. are attempting to solve the problems associated with DFMO, discussed above. Gerhart et al. note that while inhibition of ODC will slow cell division and proliferation, putrescine, and spermidine are not essential for cell viability if the pool of preexisting spermine is maintained above a critical level. These agents act to deplete intracellular levels of spermine, thereby inhibiting cell proliferation. However, as with DFMO, these reagents require directed gem-halogenation, a difficult and expensive synthesis.

Another reference by Bey et al., U.S. Pat. No. 4,935,449, describes other spermidine, and spermine derivatives which find use as polyamine oxidase (PAO) inhibitors. The compounds described by Bey et al. '449 are N-substituted 2,3-butadienyl derivatives of both spermidine and spermine. They are described as irreversible inhibitors of PAO. By inhibiting PAO, which catalyzes interconversion of the various polyamines, the formation of putrescine (formed by cleavage of $N^1$-acetylspermidine by PAO) is inhibited, thereby lowering intracellular levels of putrescine. It is believed that these PAO substrate analogs function by covalently bonding to the active site of the PAO enzyme.

As is clear from the above references, a complete understanding of the function of polyamines is far from clear. While inhibition of polyamine formation has been linked to cell growth inhibition, inducing and maintaining low intracellular levels of polyamines in proliferating cells is complicated by intercellular transport mechanisms which efficiently import polyamines such as putrescine, as well as duplicative systems for polyamine formation. Moreover, many of the above compounds contain halogen moieties, which both complicates their synthesis, and heightens their toxicity. In light of this, there is clearly the need for therapeutic agents which inhibit cell growth by interuption of polyamine synthetic pathways, compounds which are simple to manufacture and administer, which effectively inhibit cell proliferation and metastases, and which have low toxicity.

ABBREVIATIONS

For purposes of brevity and clarity, the following abbreviations shall be used throughout the specification and drawings: putrescine (Put), cadaverine (Cad), ornithine (Orn), difluoromethylornithine (DFMO), ornithine decarboxylase (ODC), dimethyl putrescine (DMP), diethyl putrescine (DEP), dibenzylpropanediamine (DBPr), dibenzylputrescine (DBP), dibenzylcadaverine (DBC), spermidine (Spd), and spermine (Spm).

SUMMARY OF THE INVENTION

In view of the above discussion, it is an aim of the present invention to provide a therapeutic treatment which inhibits the growth, proliferation, and metastases of cancer cells, neplasias, and other transformed cell lines.

It is also an aim of the present invention to provide a treatment of cancers in humans which is effective to inhibit the growth and spread of the cancer, and which is relatively low in toxicity as compared with many conventional therapeutic agents.

A further aim of the present invention is to provide a pharmaceutical unit dosage form containing suitable concentrations of the N,N'-dibenzyldiaminoalkanes described herein in combination with pharmaceutically-suitable carriers, diluents, adjuvants, fillers, binders, and the like.

The present invention includes a method of inhibiting growth of cancer cells which comprises contacting the cells with an effective growth-inhibiting amount of a compound selected from the group consisting of linear $C_2$–$C_{10}$ N,N'-dibenzyl α,ω-diaminoalkanes, branched $C_2$–$C_{10}$ N,N'-dibenzyl α,ω-diaminoalkanes, pharmaceutically-suitable salts thereof, and mixtures thereof.

The above method further includes administering an amount of the above-described compound which is effective to inhibit growth of cancer cells to a human cancer patient in need thereof.

This invention also includes a method of inhibiting growth of cancer cells which comprises contacting the cells with an effective growth-inhibiting amount of a compound selected from the group consisting of

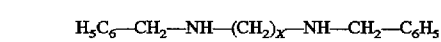

wherein X is an integer of from 3–8, pharmaceutically-suitable salts thereof, and mixtures thereof.

Additionally, the present invention further includes a pharmaceutical unit dosage form comprising an amount of a compound selected from the group consisting of linear $C_2$–$C_{10}$ N,N'-dibenzyl α,ω-diaminoalkanes, branched $C_2$–$C_{10}$ N,N'-dibenzyl α,ω-diaminoalkanes, pharmaceutically-suitable salts thereof, and mixtures thereof; in combination with a pharmaceutically-acceptable carrier, wherein said amount is effective to inhibit growth of cancer cells within a human cancer patient following administration of the dosage form to the patient.

DETAILED DESCRIPTION OF THE INVENTION

Figure 1:
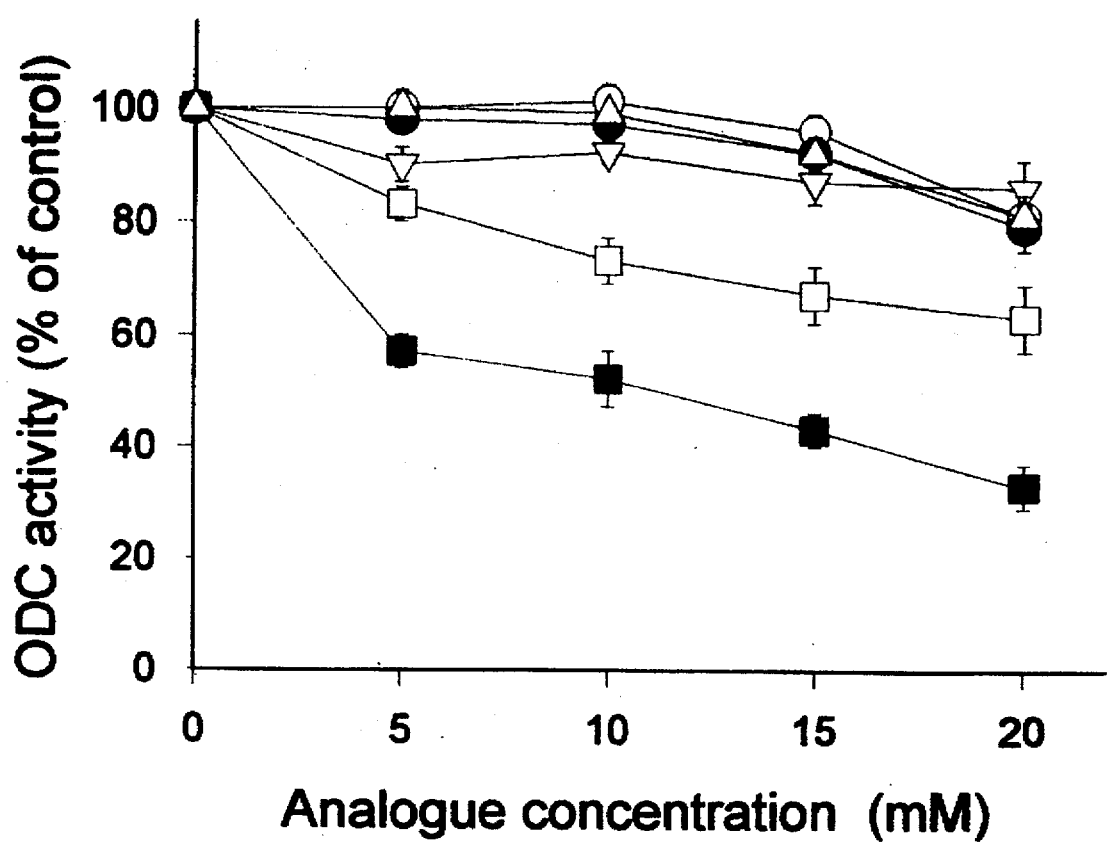
FIG. 1 is a plot of in vitro inhibition of ODC from rat hepatoma cells (Reuber H-35) by Put (■), DMP (□), DEP (♦), DBP (○), DBC (●), and DBPr (△). Ornithine concentration was 1 mM.

The present invention provides a therapeutic method of inhibiting growth of cancer cells comprising contacting the cells with an effective growth-inhibiting amount of linear and/or branched $C_2$–$C_{10}$ N,N'-dibenzyl-α,ω-diaminoalkanes. These diaminoalkanes are simple to manufacture, low in toxicity, and exhibit both in vitro and in vivo inhibition of cancer cell growth, proliferation, and metastasis.

The present invention further includes a pharmaceutical unit dosage form comprising an effective growth-inhibiting amount of the linear and/or branched $C_2$–$C_{10}$ N,N'-dibenzyl-α,ω-diaminoalkanes in combination with a pharmaceutically-suitable carrier.

As with any class of pharmaceutical compounds, treatment with some of the compounds described herein is preferred over others. From an ease of administration standpoint, treatment with compounds having the formula

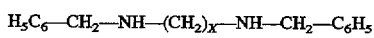

wherein X is an integer of from 3–8, and their pharmaceutically-suitable salts is preferred because these compounds are water soluble, and easily administered orally. The preferred treatment uses N,N'-dibenzylputrescine (DBP) and/or N,N'-dibenzylcadaverine (DBC). Among these two compounds, treatment with DBP is preferred.

The N,N'-dibenzyl-α,ω-diaminoalkanes of the present invention are useful both in the free amino form and in the form of their acid addition salts. The acid addition salts are merely a more convenient form for use. In practice, use of the salt amounts to use of an equivalent quantity of the free base. The term "pharmaceutically-suitable salts," or "pharmaceutically-acceptable salts" as used herein means any non-toxic organic or inorganic acid addition salt of the subject dibenzyldiaminoalkanes. Illustrative inorganic acids which form suitable salts include hydrochloric, hydrobromic, sulfuric, and phosphoric acids; and acid metal salts such as sodium monohydrogen orthophosphate and potassium hydrogen sulfate. Illustrative organic acids which form suitable salts include mono, di, and tricarboxylic acids. This group of organic acids includes such acids as acetic, glycolic, lactic, pyruvic, malonic, succinic, glutaric, α-ketoglutaric, α-ketocaproic, α-ketoisocaproic, α-ketoisovaleric, fumaric, malic, tartaric, citric, ascorbic, maleic, hydroxymaleic, benzoic, hydroxybenzoic, phenylacetic, cinnimic, salicylic, and 2-phenoxybenzoic acids. Other organic acids which form suitable salts are sulfonic acids such as methane sulfonic acid and 2-hydroxyethane sulfonic acid.

As used herein, the terms "cancer" and "cancer cells" refer to all types of cancer, including both benign and malignant tumors or neoplasms, and includes melanomas, lymphomas, leukemias, and sarcomas. Illustrative examples of cancerous tumors and tissues are cutaneous tumors, such as malignant melanomas and mycosis fungoides; hematologic tumors, such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder, or testis; soft tissue sarcomas, osseus or non-osseus sarcomas, breast tumors; tumors of the pituitary, thyroid, and adrenal cortex; gastrointestinal tumors, such as those of the esophagus, stomach, intestine, and colon; pancreatic and hepatic tumors; laryngeae papillomestasas, and lung tumors.

As used herein, "inhibiting cell growth" means slowing, interrupting, arresting, and/or terminating the growth, proliferation, and/or metastases of a rapidly proliferating tumor or transformed cell line. It is understood that inhibiting cell growth of a tumor or cell line does not necessarily provide a "cure" in the sense that the tumor tissue or transformed cells are completely destroyed.

Synthesis of the N,N'-dibenzyl-α,ω-diaminoalkanes of the present invention is very straightforward, and can be accomplished quite easily in bulk quantities. The reactant α,ω-diaminoalkanes, 1,2-diaminoethane, DBPr (1,3-diaminopropane), Put (1,4-diaminobutane), Cad (1,5-diaminopentane), hexamethylenediamine, etc. are all available commercially from numerous sources (e.g. Aldrich Chemical Co., Milwaukee, Wis., USA). Conversion to the bisbenzyl derivatives is accomplished by reaction of the diamines with benzaldehyde followed by reduction of the Schiff bases with sodium borohydride. (Samejima, K., et al. (1984), *Chem. Pharm. Bull.* 32(9):3428–3435, incorporated herein by reference.)

Product separation can be accomplished using any known method, including chromatography, distillation, and the like.

Administration of the dibenzylaminoalkanes to a human or non-human patient can be accomplished by any means known. The preferred administration route is orally. The treatment method is also amenable to parenteral administration, including intravenous administration, intraarterial administration, intratumor administration, intramuscular administration, intraperitoneal administration, and subcutaneous administration in combination with a pharmaceutical carrier suitable for the chosen administration route.

In mice, it has been shown that introduction of 0.15% DBP in drinking water, administered ad libitum, reduces the size of cell-derived rat and human xenografts by a factor of 6 to 7. The treatment also inhibits metastases of xenographic tumors from both rat cell line carcinomas and human cell line carcinomas. (See below for further discussion.)

Treatment included 0.15% DBP in drinking water over a period of four weeks, or i.p. injection (20–200 mg/kg) over a period of three weeks.

It must be noted, as with all pharmaceuticals, the concentration or amount of the N,N'-dibenzyl α,ω-diaminoalkane administered will vary widely depending upon the severity of the ailment being treated, the mode of administration, the condition of the subject being treated, and the particular dibenzyldiaminoalkane being used.

The presently described treatment can also be administered to a patient as part of a treatment regime which includes other known therapeutic methods useful for tumor therapy. For example, the N,N'-dibenzyldiaminoalkanes described herein can be administered in conjunction with surgical excision of the tumor or with radiation therapy, or the compounds can be administered in conjunction with known cytotoxic agents. By limiting growth of a tumor, the present treatment facilitates complete excision of the tumor by surgical methods, and/or complete radioactive destruction of the tumor while subjecting the patient to a smaller radiation dose. An illustrative listing of cytotoxic agents which can be used in conjunction with the present invention includes cyclophosphamide, methotrexate, prednisone, 6-mercaptopurine, procarbazine, daunorubicin, vincristine, vinblastine, chlorambucil, cytosine arabinoside, 6-thioguanine, thio TEPA, and 5-fluorouracil, among others.

The present invention also includes unit dosage forms of the dibenzyldiaminoalkanes described herein. The unit dosage forms allow easy administration of the treatment, and also ease tracking a patient's response to a given treatment regimen. This information can be used to increase or decrease the amount of compound administered to a given patient. The dosage forms may be in either solid or liquid form.

The solid unit dosage forms can be of conventional design. Solid forms include gelatin capsules containing a dibenzyldiaminoalkane as described above, and a conventional carrier. Conventional carriers often include a lubricant and inert fillers, such as lactose, sucrose, and corn starch. The compounds can also be tabletted using conventional tablet bases such as lactose, sucrose, or corn starch, in combination with a binder such as acacia, a disintegrating agent such as alginic acid, and a lubricant such as magnesium stearate.

For parenteral administration, the dibenzyldiaminoalkanes may be administered as injectable dosages of a solution or suspension of the compound in a physiologically-acceptable diluent with a pharmaceutically-acceptable sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers.

EXPERIMENTAL DETAILS AND DISCUSSION

In Vitro Inhibition of ODC

ODC was isolated from rat hepatoma cell cultures (Reuber H-35 cells) prepared in conventional fashion. Of the N,N'-di-substituted diamines assayed for ODC inhibition (DMP, DEP, DBPr, DBP, and DBC), all were weaker inhibitors than putrescine itself. The results are displayed graphically in FIG. 1. At a ratio of 15 to 1, inhibitor to substrate, ODC activity decreased 57% when the inhibitor was putrescine, 33% and 13% when the inhibitor was DMP and DEP, respectively; and less that 10% when the dibenzyl derivatives DBPr, DBP, and DBC were used.

In Vitro Effect on Cell Proliferation

Figure 2:
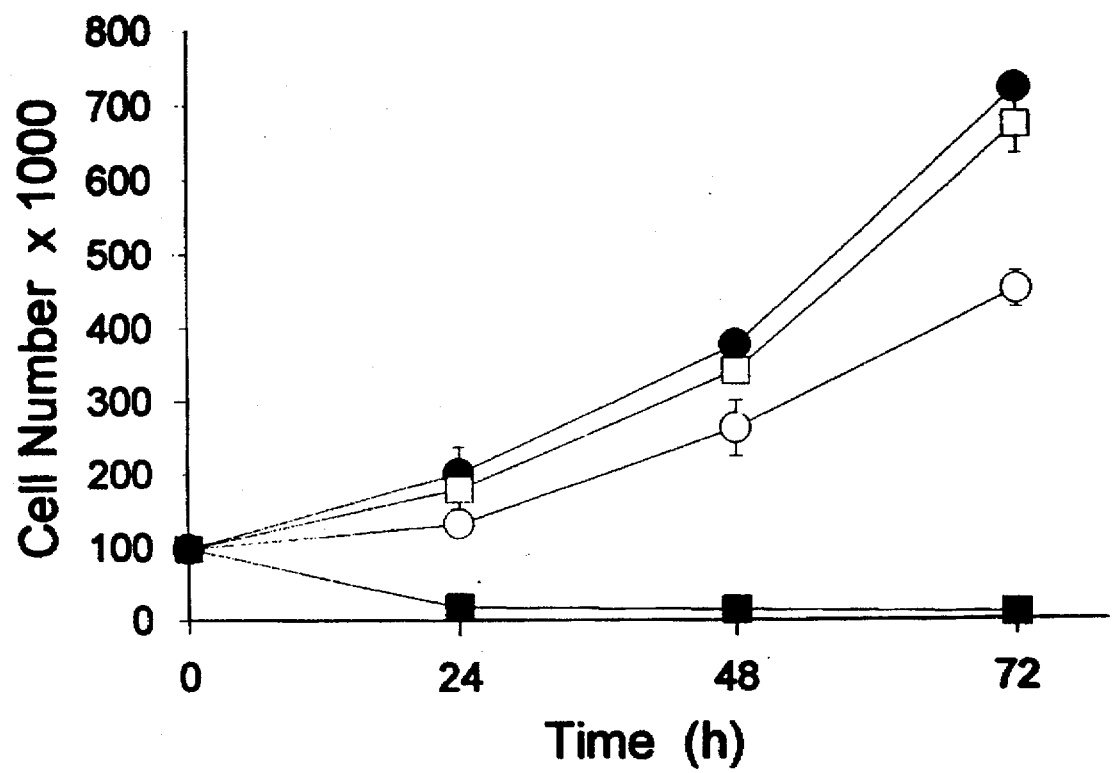
FIG. 2 is a plot of the effect over time of DMP (○), DEP (□), and DBP (♦) on proliferation of rat H-4-II-E hepatoma cells. Control (●).

Results here are depicted in FIG. 2. Rat hepatoma cells H-4-II-E were cultured in conventional fashion, and then DMP, DEP, and DBP added at a concentration of 1 mM. Incubation of the cultures was carried out in standard fashion in the presence of 1 mM aminoguandine, an inhibitor of polyamine oxidases (PAO). As is clear from FIG. 2, at 24 hours after addition, DBP had inhibited cell growth. Even before the cytotoxic effect of DBP was evident, after only one hour, DBP had already induced the formation of vacuoles in the cells, altered their morphology, and loosened the cells from the plate surface. DEP and DMP behaved as weak inhibitors of cell proliferation, and had no effect on cell morphology.

Figure 3:
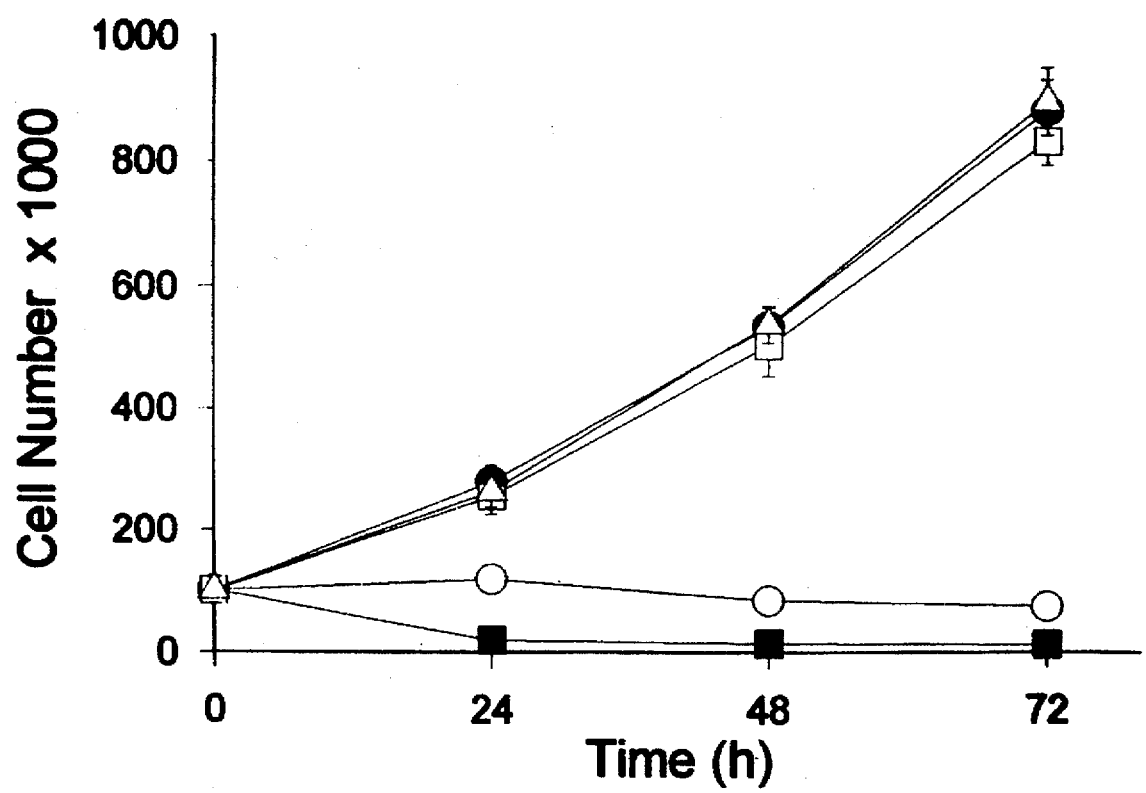
FIG. 3 is a plot of the effect of different concentrations of DBP on proliferation of rat H-4-II-E hepatoma cells. Control (●), 1 mM DBP (♦), 100 μM DBP (○), 10 μM DBP (□), 1 μM DBP (△).

The inhibitory effect of different concentrations of DBP was then explored. Graphic results are shown in FIG. 3. Here, DBP was added to the cultures in the following concentrations: 1 mM, 100 µM, 10 µM, and 1 µM. It is obvious from FIG. 3 that at a concentration of only 100 µM, DBP has a marked inhibitory effect on cell proliferation.

Figure 4A:
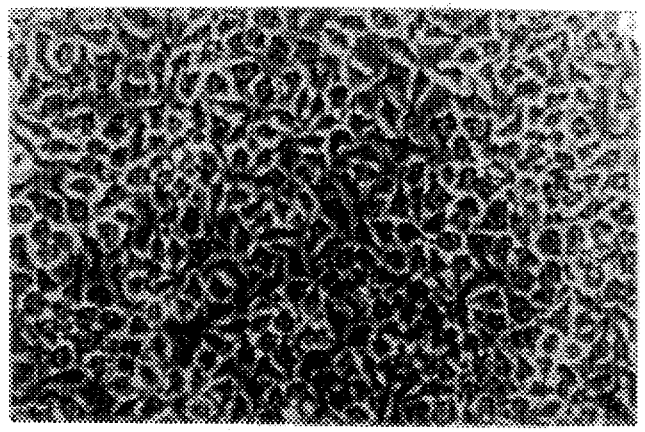
FIG. 4 is a series of photomicrographs showing the effects of DBP on cell morphology of rat H-4-II-E hepatoma cells. Photo A is a control run, photo B is at 100 μM DBP, and photo C is at 10 μM DBP.
Figure 4B:
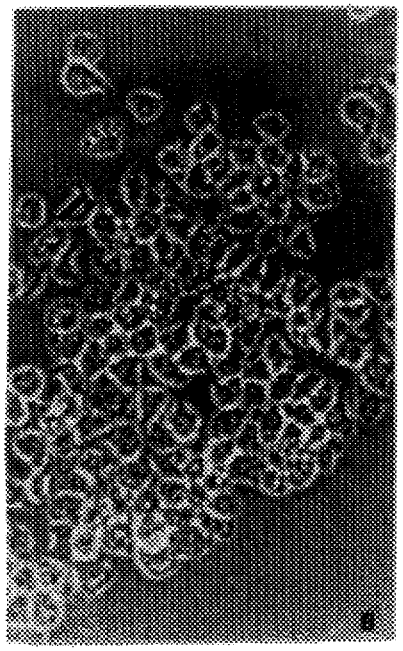
Figure 4C:
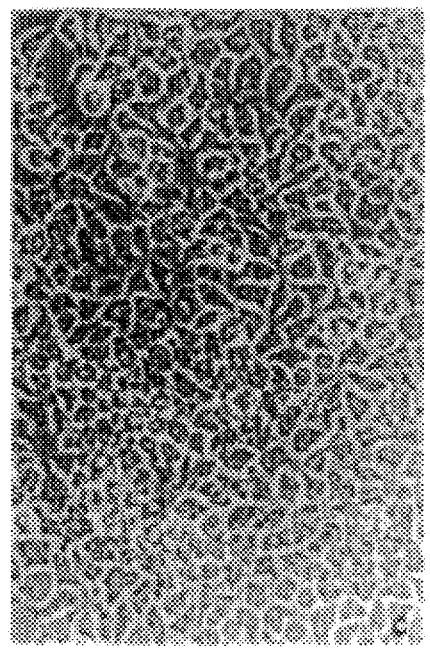
Figure 6:
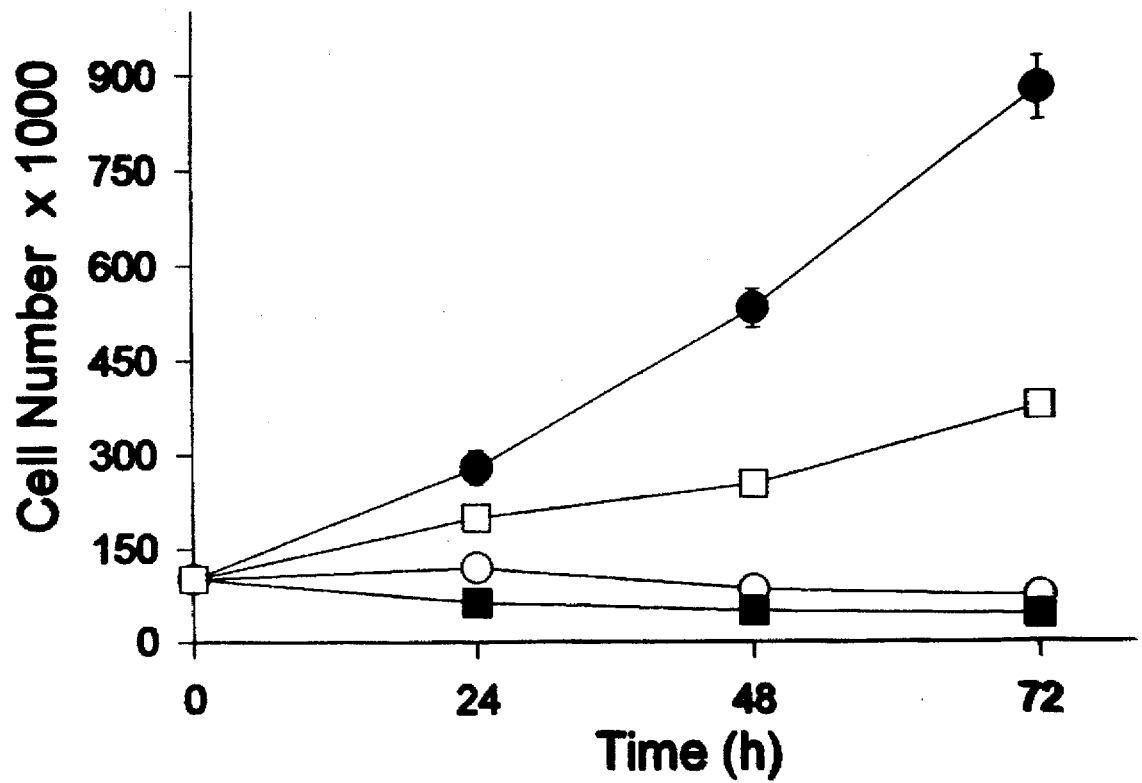
FIG. 6 is a plot showing proliferation of rat H-4-II-E hepatoma cells incubated with 100 μM DBP (○), DBC (■), and DBPr (□). Control (●).
Figure 7A:
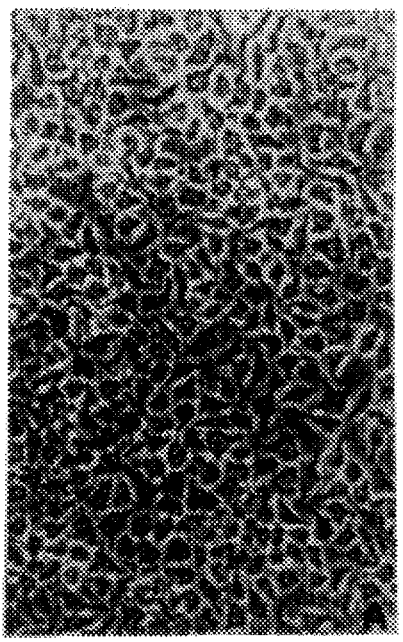
FIG. 7 is a series of photomicrographs showing the effects of DBP (Photo B), DBC (Photo C), and DBPr (Photo D) on rat H-4-II-E hepatoma cells. Control run (Photo A).
Figure 7B:
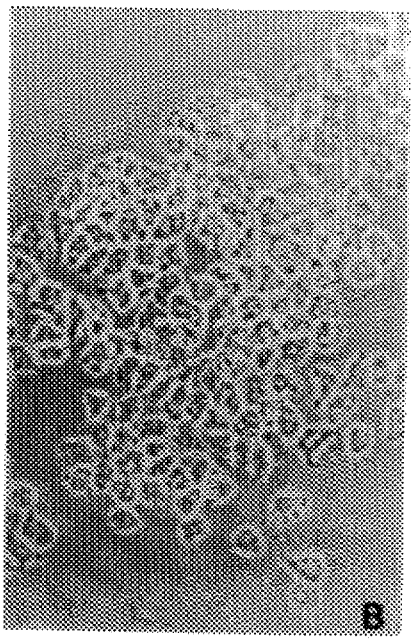
Figure 7C:
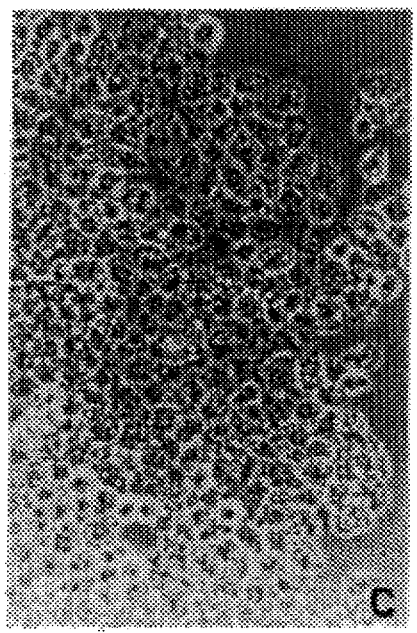
Figure 7D:
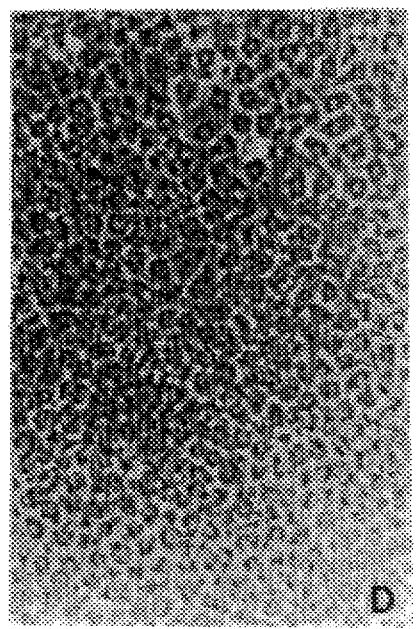

The effect of DBP on cell morphology is shown in FIG. 4. The photomicrographs shown here were taken 24 hours after addition of DBP to the cultures using a contrasting-phase microscope (×160) with a blue filter. FIG. 4A shows a control run, FIG. 4B shows a run at 100 µM DBP, and FIG. 6C shows a run at 10 µM DBP. The cells shown in 4B (100 µM DBP) are clearly different in morphology from the control run (4A). The cells shown in 4C (10 µM DBP), however, still adhered to the plate surface, and remained viable.

Figure 5:
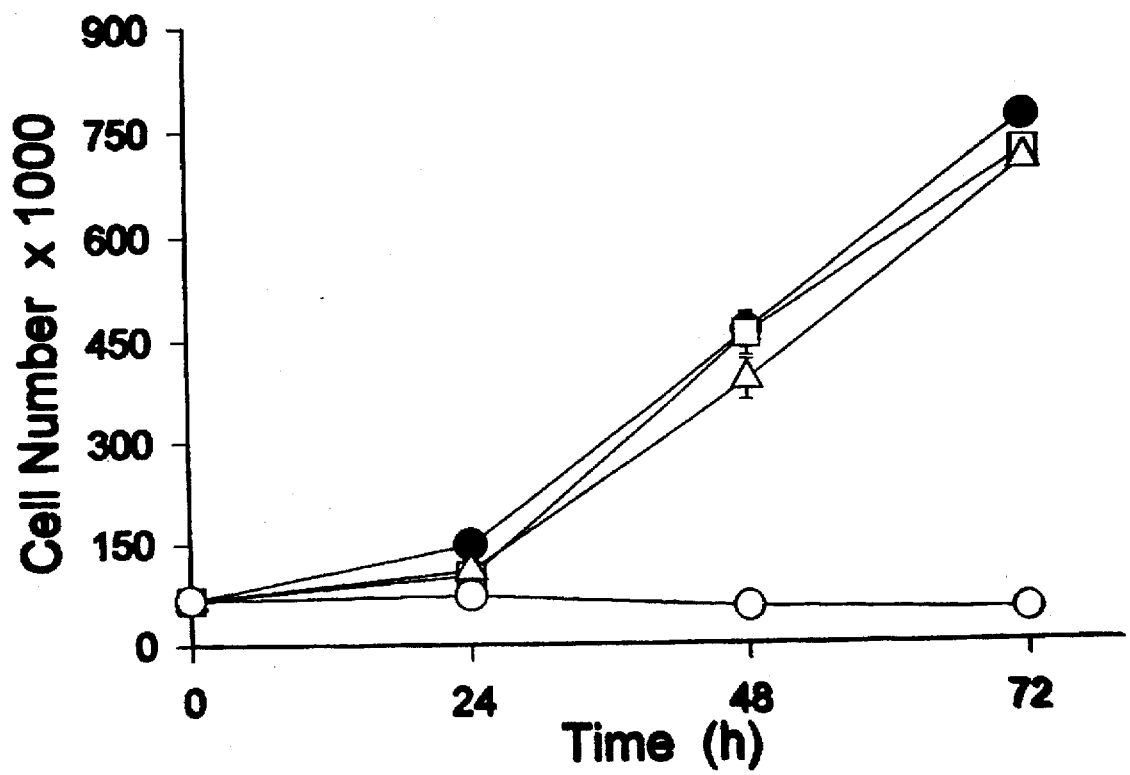
FIG. 5 is a plot showing proliferation of rat H-4-II-E hepatoma cells incubated with 100 μM DMP (□), DEP (△), and DBP (○). Control (●).

Cell proliferation studies were also conducted to analyze the effect of the terminal groups on cell inhibition. Cultures were incubated in the presence of 100 µM DBP, DMP, and DEP. The results are depicted graphically in FIG. 5. While DMP and DEP were without effect at this concentration, DBP was found to inhibit proliferation at 24 hours. 48 hours after incubation, DBP is shown to significantly reduce the number of cells in culture.

Comparative proliferation studies were also carried out to study the effect of chain length on the inhibitory effect of N,N'-dibenzylaminoalkanes. (See FIG. 6.) The in vitro inhibitory effects of DMP, DMC, and DBPr, were studied in the same rat H-4-II-E hepatoma cells as the above experiments. Here, cells were incubated in the presence of 100 µM DBP, DBC, and DBPr. All three homologs showed inhibition of cell proliferation.

FIG. 7 is a series of photomicrographs (×160) of the above homologous cultures. The photomicrographs were taken 24 hours after introduction of the dibenzyldiaminoalkanes. DBC and DBP, photos 7B and 7C, respectively, affect cell morphology similarly, while DBPr, photo 7D, affected cell morphology to a lesser extent. Photo 7A is the control culture.

In Vitro Effect on Putrescine Uptake

A study was also performed to examine if DBP, DBC, and DBPr affected the in vitro uptake of extra-cellular putrescine by H-4-II-E hepatoma cells. Recall that treatment with DFMO results in increased putrescine uptake by cells so treated.

Figure 8:
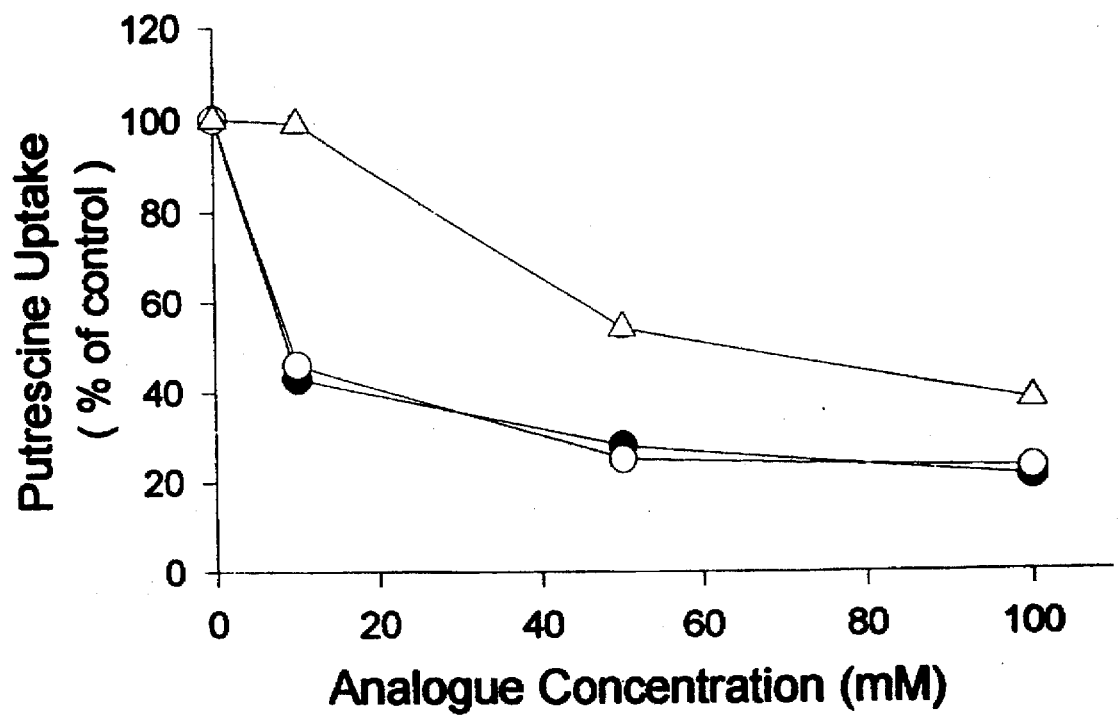
FIG. 8 is a plot showing inhibition of uptake of $(1,4-^{14}C)$-Put in rat H-4-II-E hepatoma cells by DBP (●), DBC (○), and DBPr (♦).

(1,4-$^{14}$C)-putrescine (10 µM) was added to the culture medium, and radioactivity measured in the cells (dpm/10 µg of protein). Uptake by control cells was considered to be 100%. As shown in FIG. 8, addition of DBP, DBC, and DBPr produced an inhibition of the uptake of exogenous putrescine. The abscissa represents the concentration of the added DBP, DBC, and DBPr. DBP and DBP produced a marked inhibition of the uptake of exogenous putrescine when the putrescine to dibenzyldiaminoalkane ratio in the culture medium is 1:1.

Figure 9:
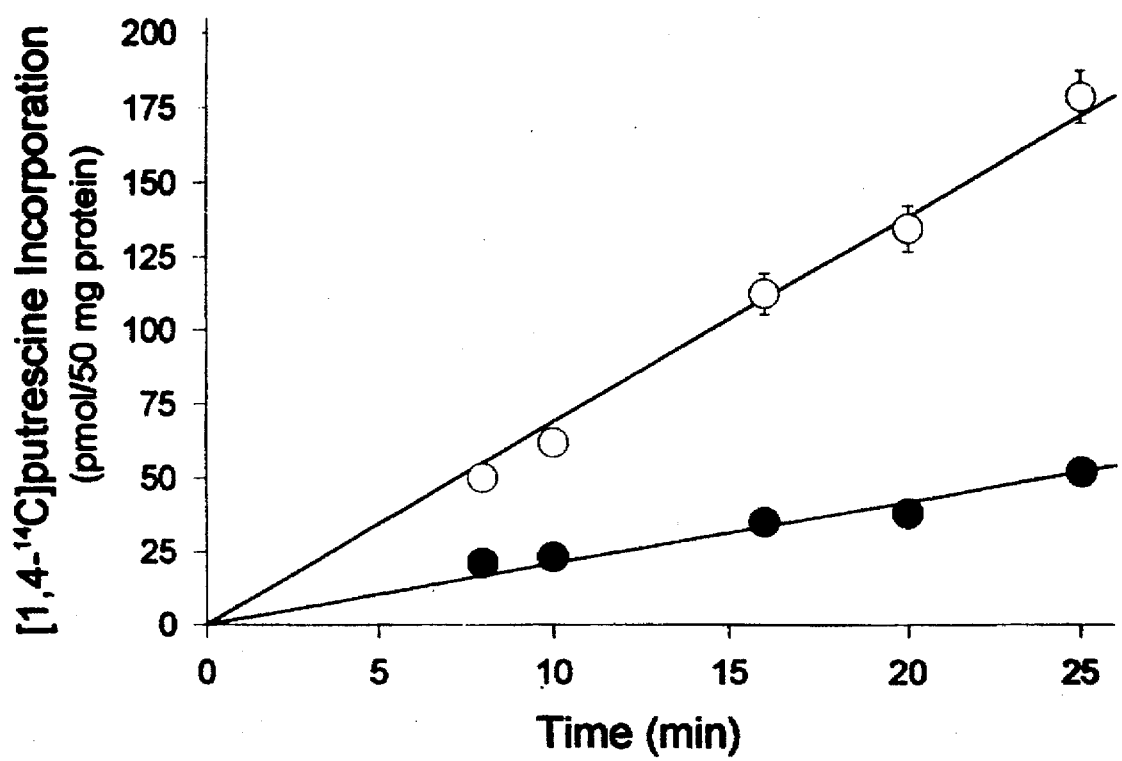
FIG. 9 is a plot of the uptake of $(1,4-^{14}C)$-Put in rat H-4-II-E hepatoma cells as a function of time. Concentration of $(1,4-^{14}C)$-Put: 2 mM (●), 20 mM (○).

Because putrescine uptake by cells is regulated by an active transport system, its $K_m$ was determined for the H-4-II-E hepatoma cell line. The uptake of (1,4-$^{14}$C)-putrescine was determined at two different putrescine concentrations as a function of time. The results are shown in FIG. 9.

Each value of the plot was corrected by subtracting the amount of label due to non-specific binding to the cell membranae. Using 2 mM and 20 mM (1,4-$^{14}$C)-putrescine concentrations, a $K_m$ of 5.2±0.6 µM was determined for the active transport. Based on this information, 15 minute incubation periods were used to study the competition of putrescine uptake versus DBP uptake, because at this time, the velocity of putrescine uptake is constant. It was thus determined that the uptake of putrescine is competitively inhibited by DBP with a $K_i$ of 6.5±1.7 µM.

Figure 10:
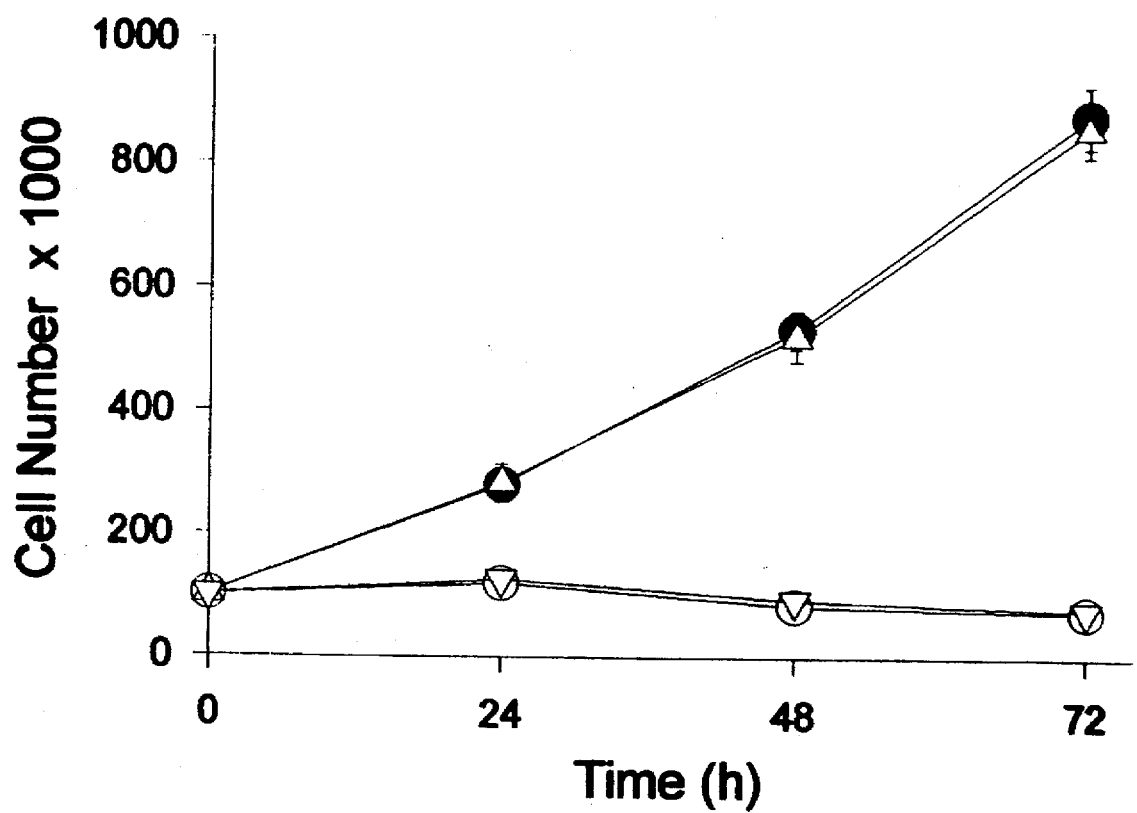
FIG. 10 is a plot of the proliferation of rat H-4-II-E hepatoma cells treated simultaneously with DBP (○), Put (△), DBP+Put (♦). Control (●).

To establish how mutual competition between DBP and putrescine affects the uptake of DBP, cells were incubated in the presence of a tenfold excess of putrescine of DBP (1 mM Put versus 100 µM DBP). Results are shown graphically in FIG. 10. The plot clearly shows that the tenfold excess of putrescine could not prevent the inhibitory effect of DBP on cell proliferation. Moreover, addition of putrescine to cultures 24 hours after introduction of DBP did not reverse the inhibitory effect of DBP (data not shown). This property of DBP is very encouraging for its therapeutic use as an antiproliferative drug, given the well-known role played by extra-cellular putrescine uptake in reverting the inhibitory effect on ODC of irreversible ODC inhibitors such as DFMO.

Comparison of the In Vitro Inhibitory Effects of DBP and DFMO

As discussed above, DFMO is a well known, and extensively investigated polyamine analog used in anticancer research. DFMO inhibits ODC activity by binding to the active site of the enzyme in an irreversible manner. It is the paragon of the so-called "suicide" inhibitors. It acts by inhibiting the intracellular production of putrescine, and therefore the intracellular production of putrescine catabolites spermidine and spermine. However, as noted hereinabove, cells treated with DFMO readily import putrescine from the extra-cellular milieu.

Figure 11:
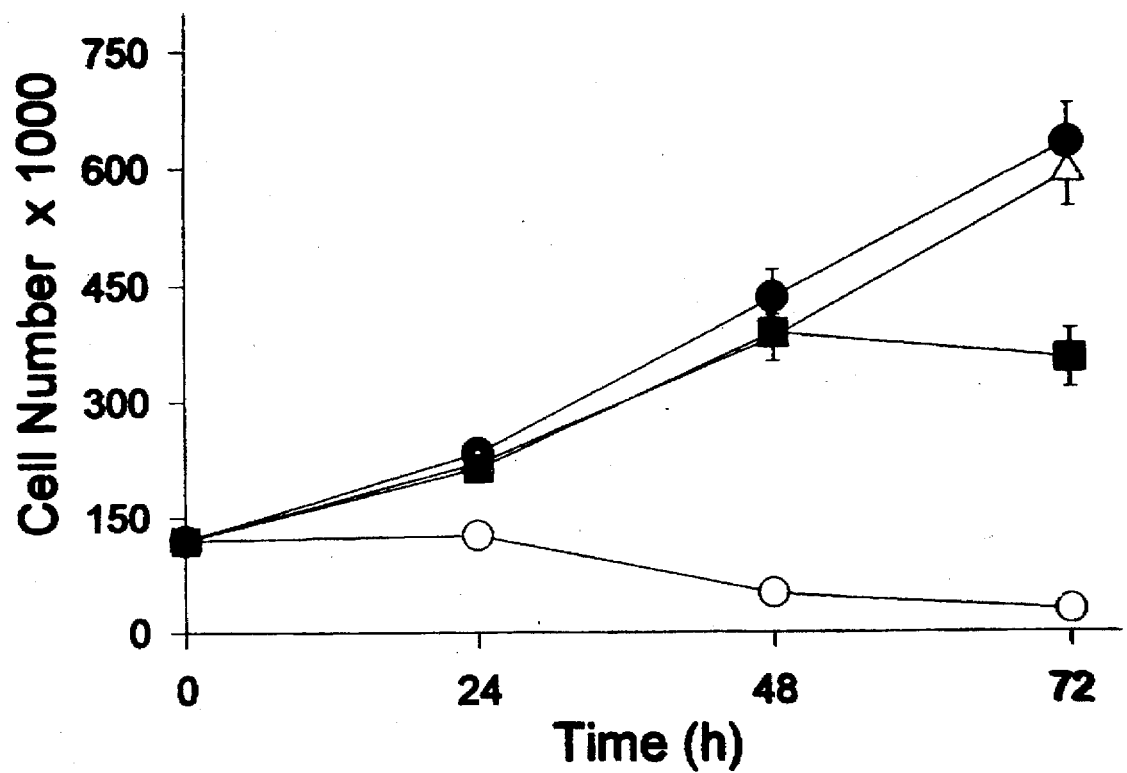
FIG. 11 is a plot of the effect of DBP and DFMO on proliferation of rat H-4-II-E hepatoma cells. 100 μM DBP (○), 100 μM DFMO (△), 1 mM DFMO (■), control (●).
Figure 12A:
FIG. 12 is a series of photomicrographs showing the effect of DBP and DFMO on the morphology of rat H-4-II-E hepatoma cells. Photo A is a control run, photo B is at 100 μM DBP, photo C is at 10 μM DFMO, and photo D is at 1 mM DFMO.
Figure 12B:
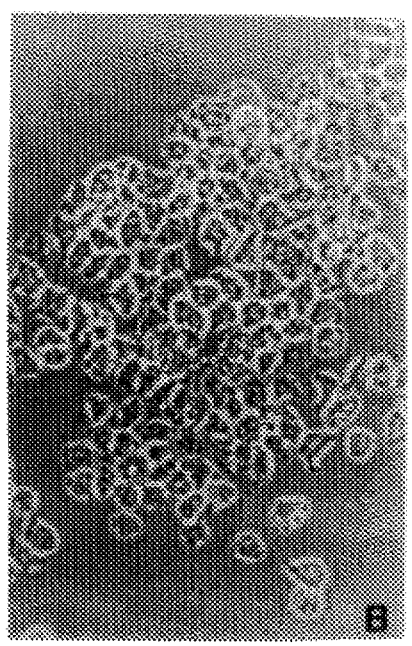
Figure 12C:
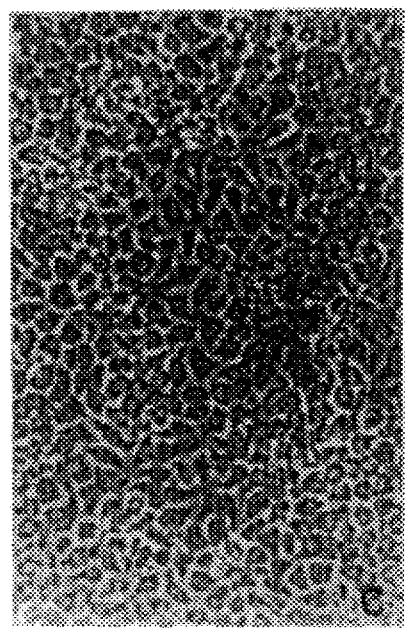
Figure 12D:
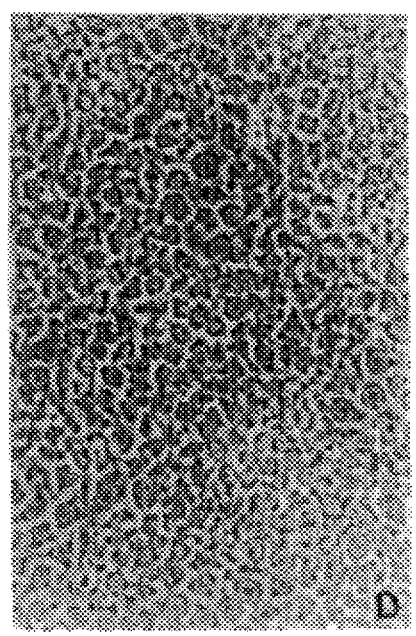

When DFMO is added to cultures of the aforementioned hepatoma cell line at a concentration of 1 mM, it was found to inhibit cell proliferation after 48 hours (see FIG. 11). However, at a concentration of 100 µM, DFMO is ineffective in inhibiting cell proliferation. In comparison, at 100 µM concentration, DBP is shown to be cytostatic after 24 hours, and cytotoxic after 48 hours.

FIG. 12 is a series of photomicrographs (×160) showing the morphology of the cells treated with DFMO and DBP as discussed immediately above. Photo 12A is a control. Photo 12B shows the DBP culture. Here, cell morphology is profoundly affected by the presence of DBP. In contrast, photos 12C and 12D, showing cells treated with DFMO 100 µM and 1 mM, respectively, show no morphological changes caused by DFMO. Here, DFMO is clearly acting as a cytostatic agent.

In Vitro Effect of DBP on Human Melanoma Cell Line (IIB-Mel-J)

Figure 13:
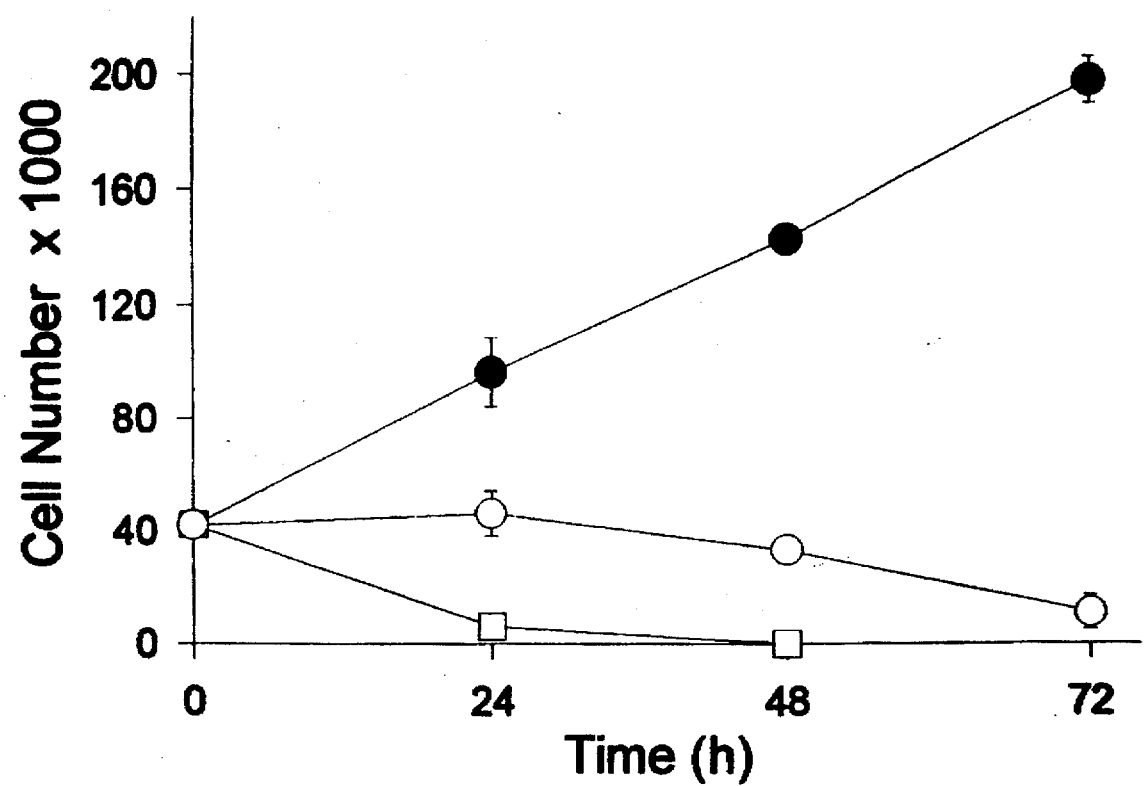
FIG. 13 is a plot showing the effect of DBP on proliferation of human IIB-Mel-J melanoma cells. 100 μM DBP (○), 1 mM DBP (□), control (●).

The effect of DBP at concentration of 100 µM and 1 mM on the human melanoma cell line IIB-Mel-J was investigated in the same manner as the hepatoma cell lines described above. Tissue cell cultures were prepared in conventional fashion, well known to those skilled in the art. The results are shown graphically in FIG. 13.

At a concentration of 1 mM, cell viability was virtually destroyed 24 hours after addition of DBP. The effect appears to be cytotoxic. At the tenfold smaller concentration of 100 µM, the inhibitory effect is less pronounced at 24 hours after incubation, but cell proliferation was markedly inhibited 72 hours after inhibition.

In Vitro Effect of DBP on DNA Synthesis and Protein Synthesis in Hepatoma Cells

Figure 14:
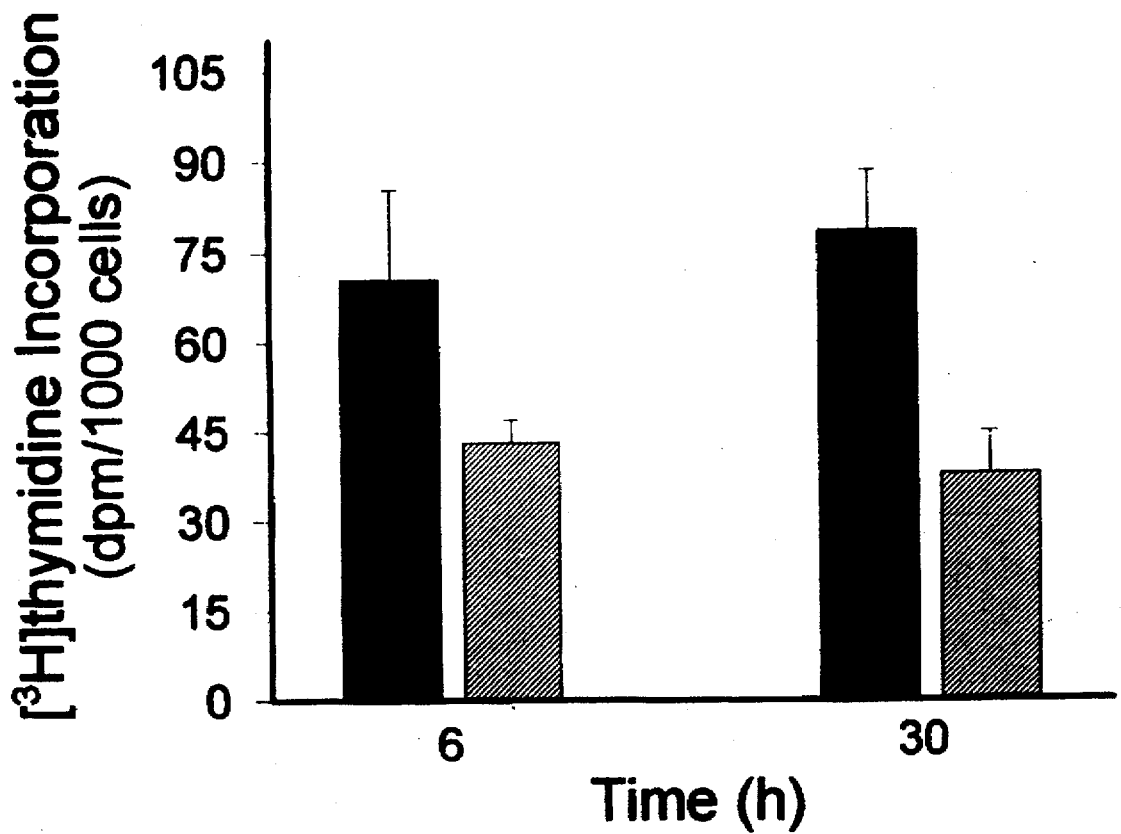
FIG. 14 is a bar graph showing the effect of DBP on ($^3$H)-thymidine uptake in rat H-4-II-E cells. Solid bar is control, hatched bar is in presence of DBP.

DNA synthesis was evaluated by the uptake of ($^3$H)-thymidine from the culture medium. DBP was used at a concentration of 100 µM. Six hours post-incubation, differences were already detected between the controls and the treated cells: In the control cells, incorporation of the labeled thymidine into cellular DNA was 44% higher than the cells incubated in the presence of DBP. After 30 hours, the DBP-treated cells had incorporated only about half the amount of labeled thymidine as the control cells. See FIG. 14.

Figure 15:
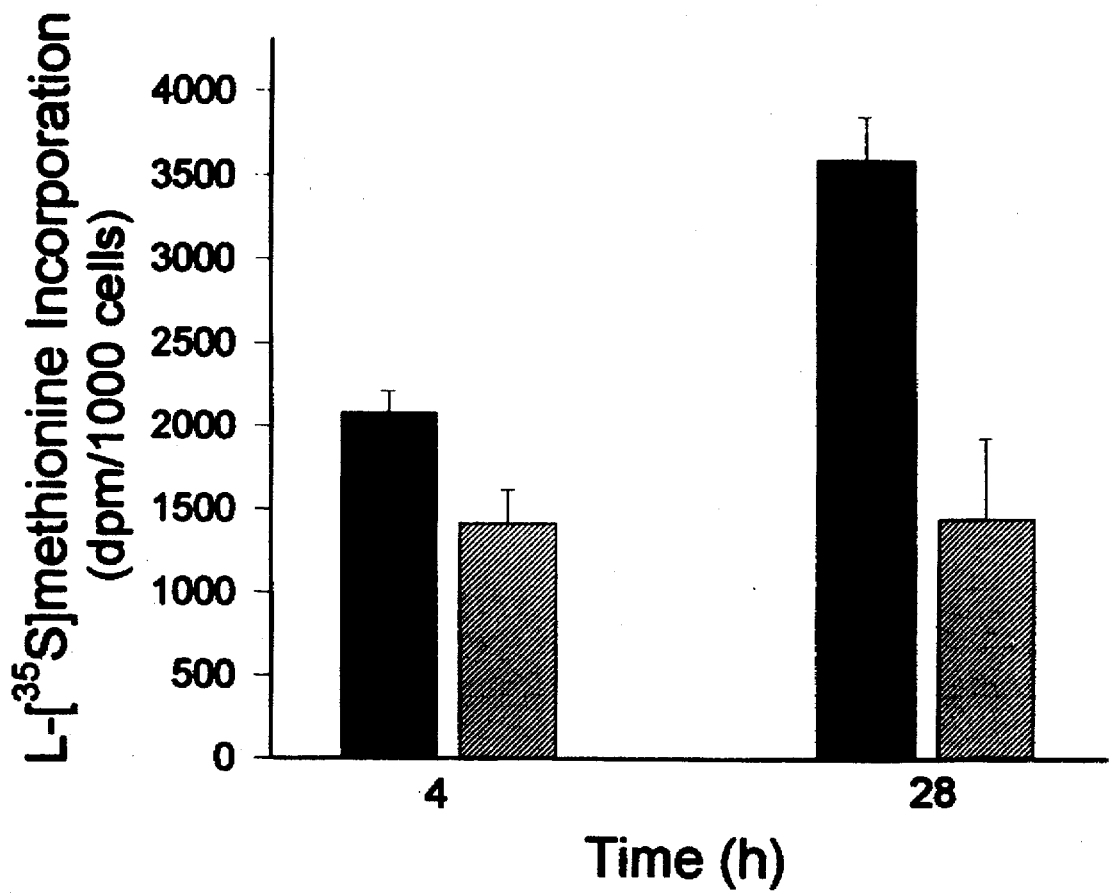
FIG. 15 is a bar graph showing the effect of DBP on (35S)-methionine uptake in rat H-4-II-E hepatoma cells. Solid bar is control, hatched bar is in presence of DBP.

Protein synthesis in the cells was measured by addition of (35S)-methionine to the cell culture medium. The results are shown in FIG. 15. After 4 hours, the DBP-treated cells exhibited 32% less label incorporation that the control groups. After 28 hours, treated cells displayed only 40% of the label uptake as the controls. As in the DNA experiment, directly above, DBP concentration was 100 μM. The increase in the amount of label uptake in the control cells with time is due to the control cells entering the exponential growth phase.

In Vitro Effect of DBP on the Endogenous Levels of Polyamines

It is known that in hepatoma H-35 cells, ODC activity is very low in quiescent cells, and is increased by the addition of $10^{-6}$M insulin, reaching a peak approximately 4 to 5 hours after the addition of the insulin. (See Frydman et al. (1991), Mol. Cell. Biochem. 100:9–23, incorporated in its entirety herein by reference.) The increase in the ODC activity is reflected in an increase in the polyamine levels within the H-35 cells. On average, the intracellular concentrations of putrescine, spermidine, and spermine double upon administration of insulin.

Figure 16:
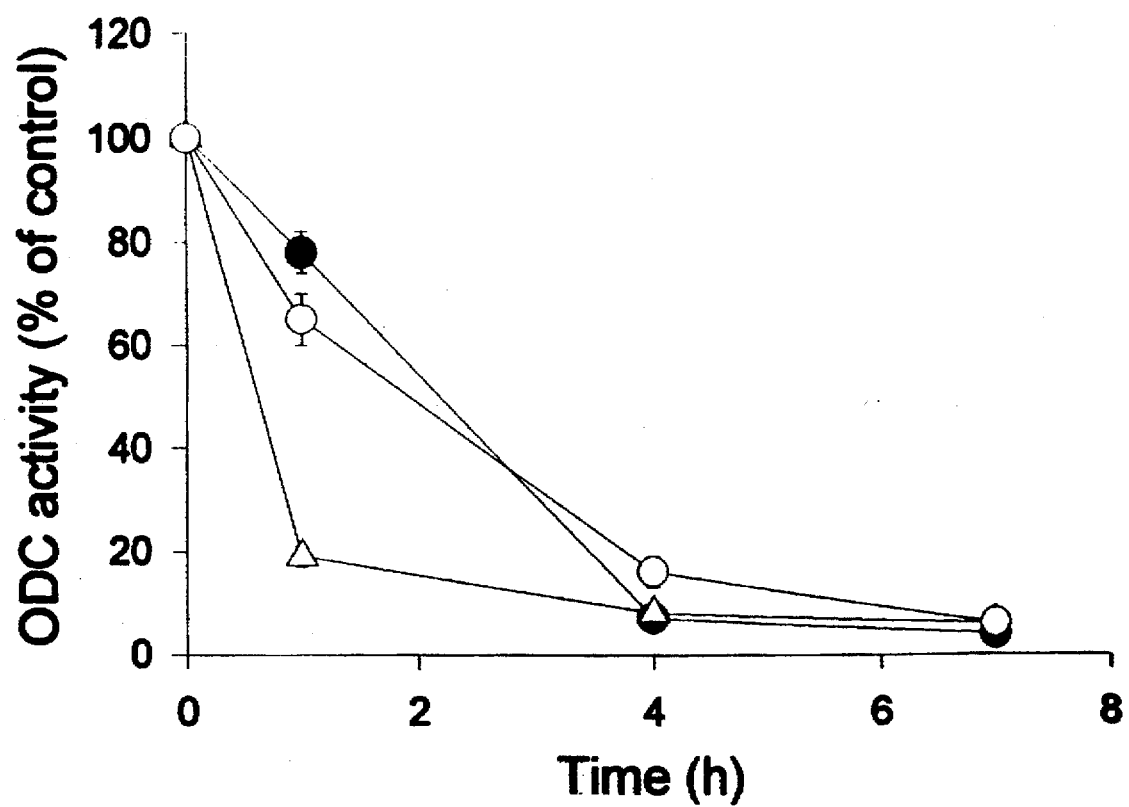
FIG. 16 is a plot of the effect of Put (●), DBP (○), and DFMO (▽) on ODC activity in insulin-induced H-35 hepatoma cells.

The activity of ODC was measured within insulin-induced H-35 cells 1, 4, and 7 hours after the addition of 100 μM putrescine (the reaction product), DBP, and DFMO. The results are shown in FIG. 16. In these runs, ODC induction peaked 7 hours after insulin addition.

When DFMO was added 1 hour before harvesting (6 hours after insulin induction), ODC is already inhibited 79% from the control group (FIG. 16, time: 1 hour). Putrescine and DBP required longer time periods to reach similar ODC inhibition levels.

When DFMO, DBP, and DBC were added 3 hours after insulin addition (4 hours before ODC reaches its peak activity, time: 4 hours), ODC inhibition values were very similar. When the three compounds were added simultaneously with insulin, no significant ODC activity was detected.

Figure 17A:
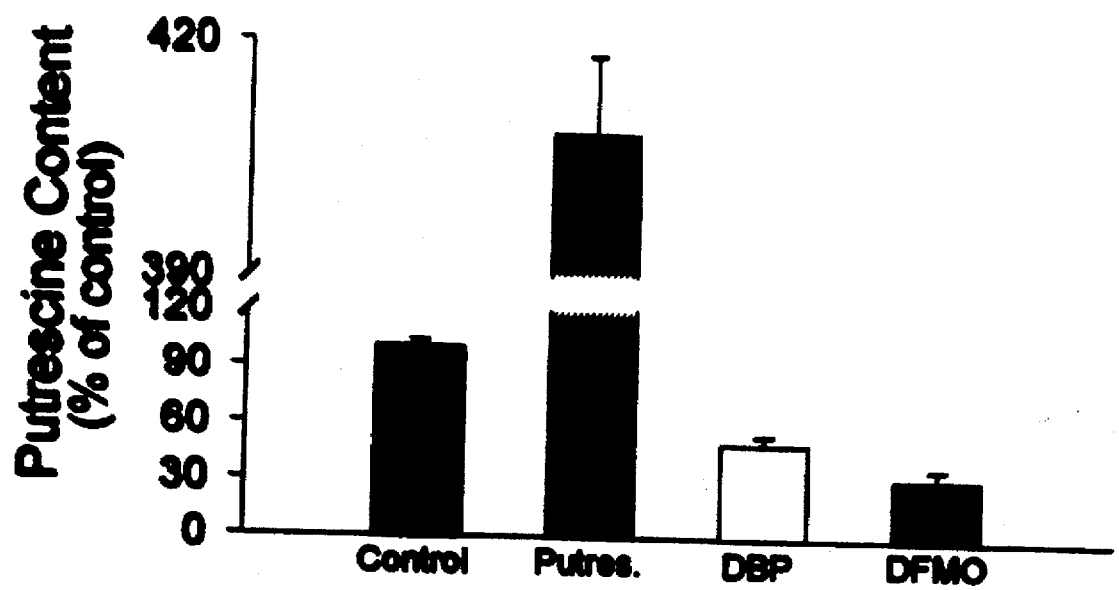
FIG. 17 is a series of bar graphs showing the effects of 100 μM Put, DBP, and DFMO on Put, Spd, and Spm levels in insulin-induced H-35 hepatoma cells.
Figure 17B:
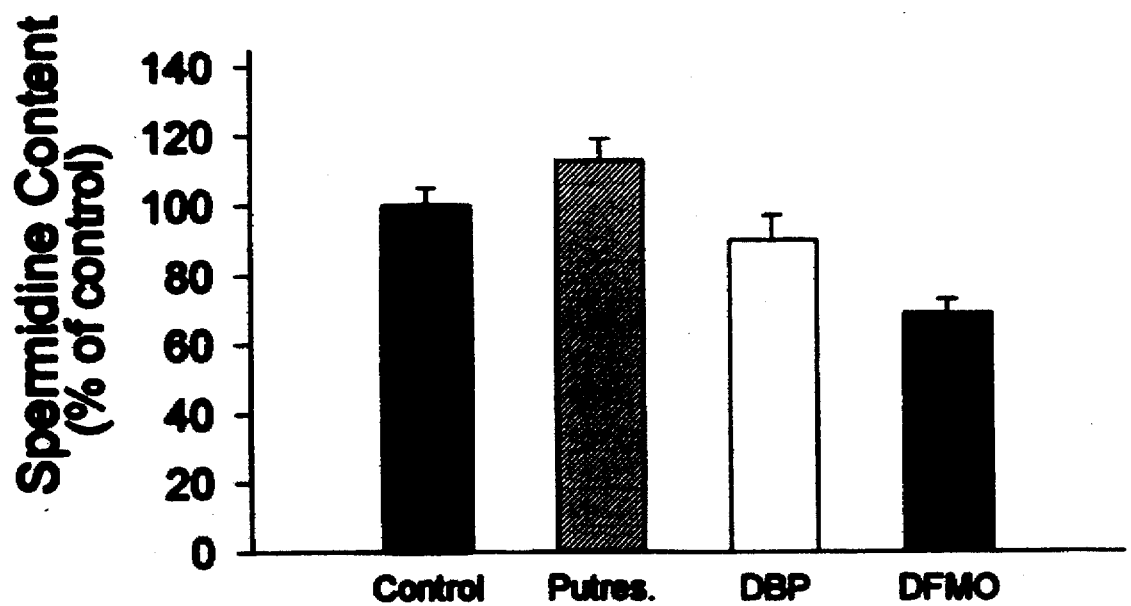
Figure 17C:
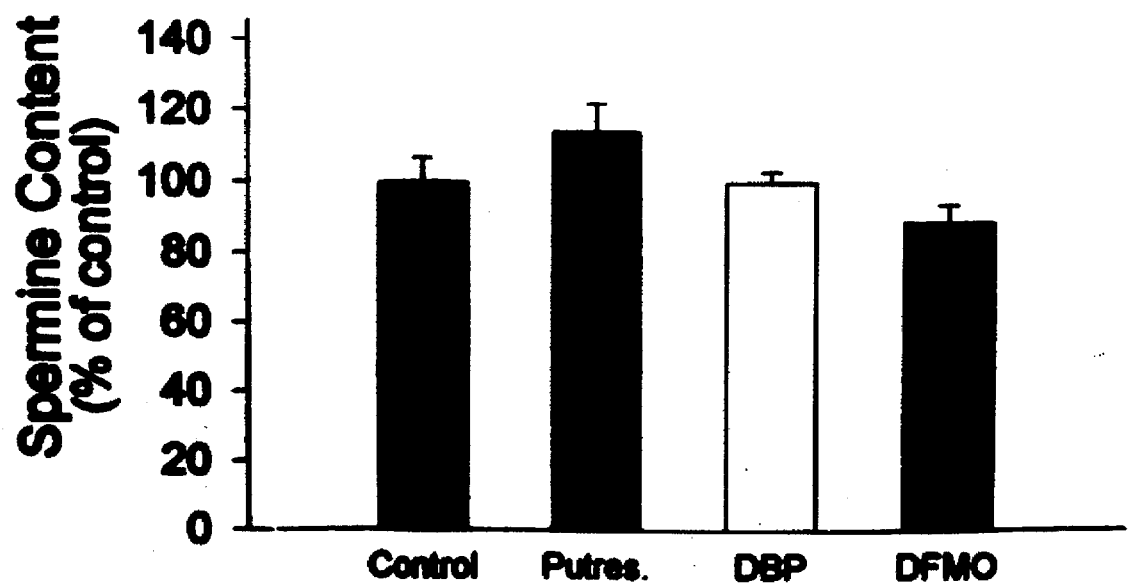

FIG. 17 shows the effect of the same experiment on intracellular polyamine levels. When measured at hour 4 as shown in FIG. 16 (i.e., 3 hours after insulin induction), it was found that both DMP and DFMO had decreased the endogenous levels of putrescine. However, only DFMO lowered the levels of spermidine. Neither reagent had an effect on the intracellular concentration of spermine.

Putrescine addition to the medium greatly increased the putrescine cell contents, as would be expected from known putrescine uptake. However, putrescine uptake had very little effect on intracellular spermidine and spermine levels. DBP uptake was approximately 13±4% of the amount of putrescine added to the medium.

Figure 18:
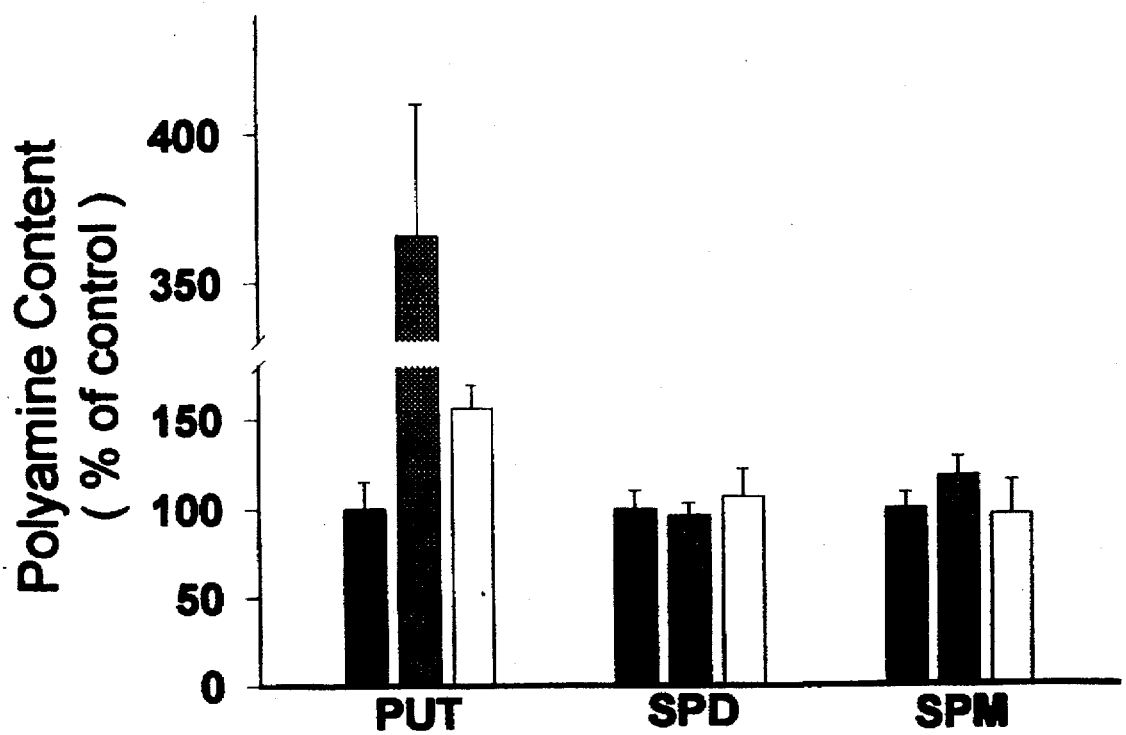
FIG. 18 is a bar graph showing Put, Spd, and Spm levels in H-35 hepatoma cells treated with DBP over 24 hours. Solid bar is control, hatched bar is 100 μM DBP, white bar is 10 μM DBP.

A parallel experiment was run using H-35 cells which were not treated with insulin. Here, the results were quite different. An experiment analogous to the experiments shown in FIGS. 3 and 4 was prepared. DBP (100 μM) was added to the cell cultures, and the cells harvested 24 hours later. By that time, cell proliferation had already stopped, and the morphology of the cells was significantly altered. Analysis showed that under these conditions, ODC activity decreased to only 3% of that found in control runs. See Table 1, below. However, while ODC activity had decreased significantly, the intracellular putrescine content was 3.6 times higher (see FIG. 18).

It is highly unlikely that this increase is due to oxidative debenzylation of DBP to putrescine due to the activity of PAO because this experiment, like the other experiments, was run in the presence of 1 mM aminoguanidine, a PAO inhibitor. DBP uptake in these experiments was approximately 6±2% of the amount added.

TABLE 1

| | ODC Activity in Hepatoma Cells Treated with DBP (100 μM) During 24 Hours | |
|---|---|---|
| | Specific Activity (nmol $^{14}CO_2$/mg protein/hr) | % Activity |
| Control | 1.45 ± 0.08 | 100 |
| DBP | 0.05 ± 0.01 | 3 |

An analysis of the intracellular distribution of DBP in these cells showed that most of the DBP (97%) was found in the cytosol, 2% was found in the nuclear fraction, and 1% in the microsomal fraction.

In Vitro Effect of DBP on a Human Brain Tumor Cell Line

Figure 19A:
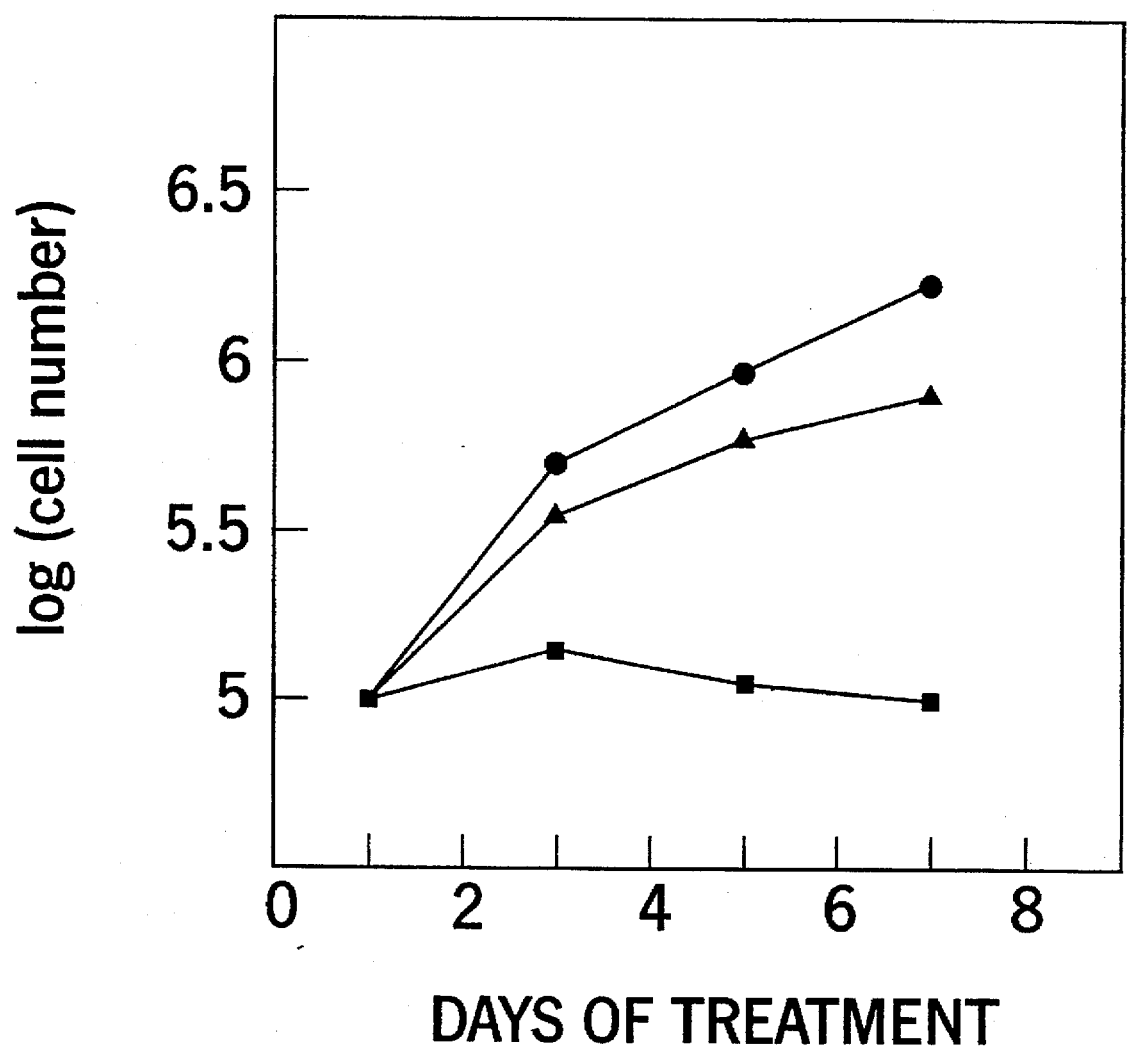
FIG. 19 is a pair of parallel plots showing the effect of DBP and DMP on the growth of human brain tumor cells U-251-MG. Control (●), 50 μM polyamine (▲), 100 μM polyamine (■).
Figure 19B:
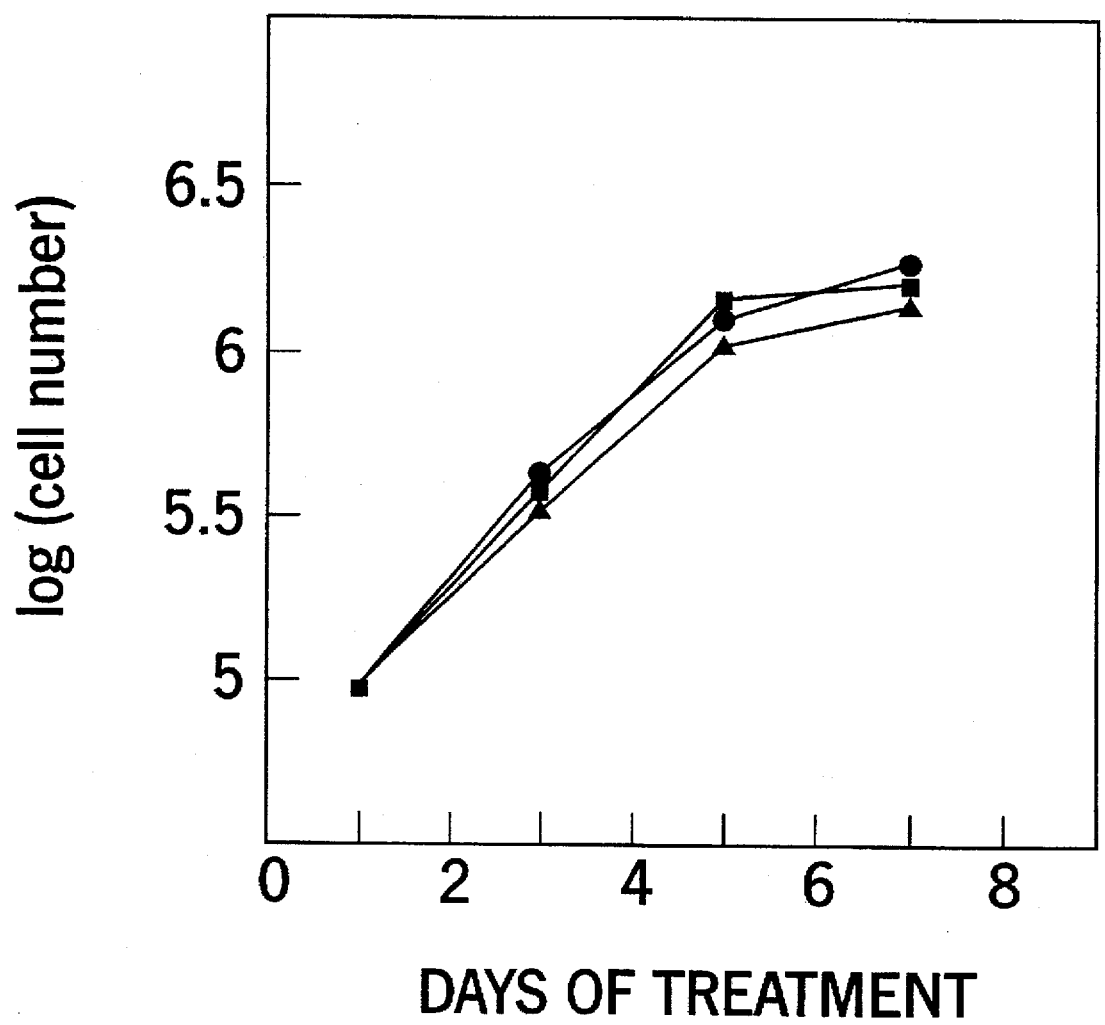

The inhibitory effect of DBP on the human brain tumor cell line U-251-MG was examined. (U-251-MG cell line graciously provided by Dr. L. Marion, Brain Tumor Research Center, University California San Francisco.) At the usual concentration of 100 μM, DBP strongly inhibited cell growth, while DMP was without effect (FIG. 19).

Figure 20A:
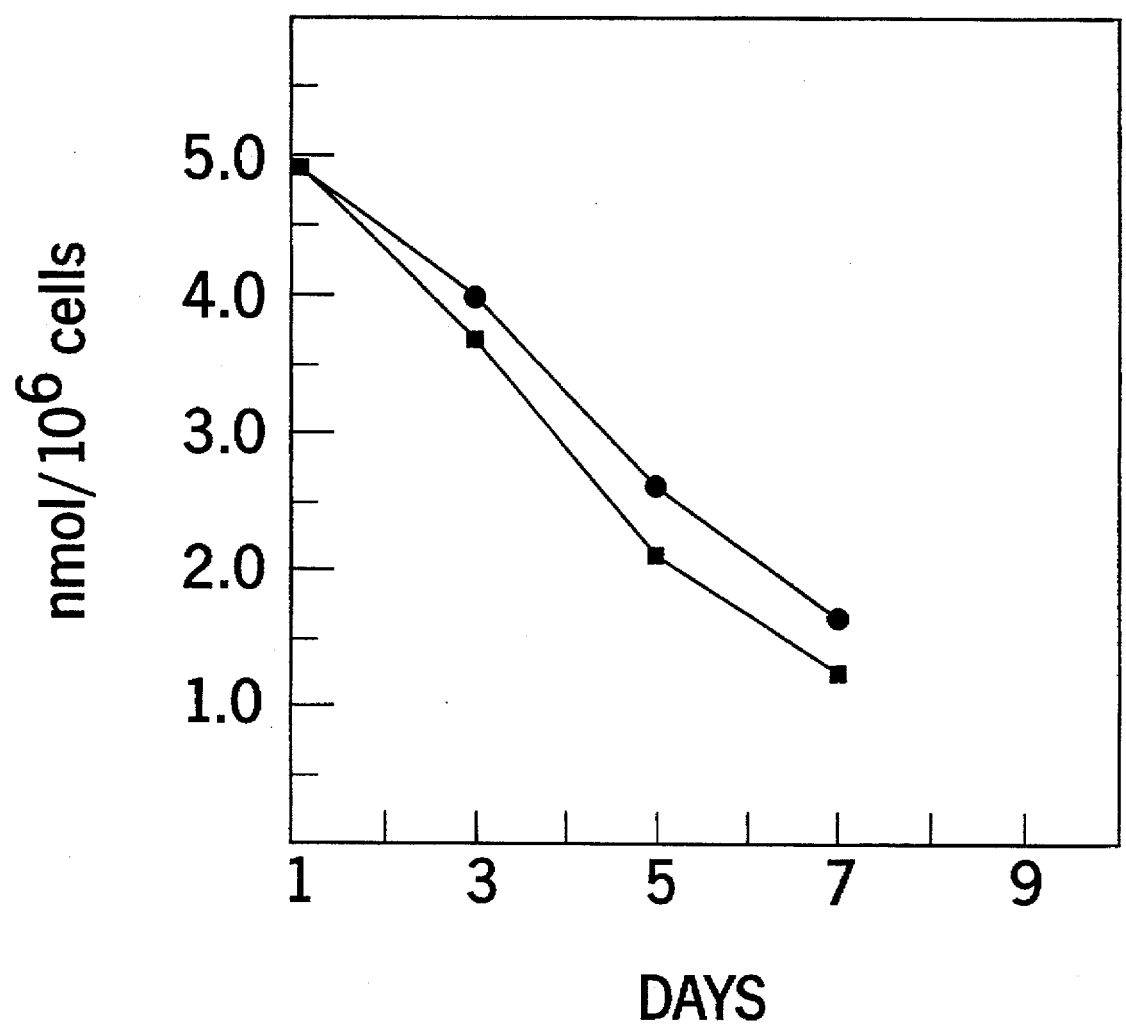
FIG. 20 is three parallel plots showing time-evolution of relative concentrations of intracellular Put, Spd, and Spm in U-251-MG human brain tumor cells in the presence and absence of DBP. Control (●), 100 μM DBP (■).
Figure 20B:
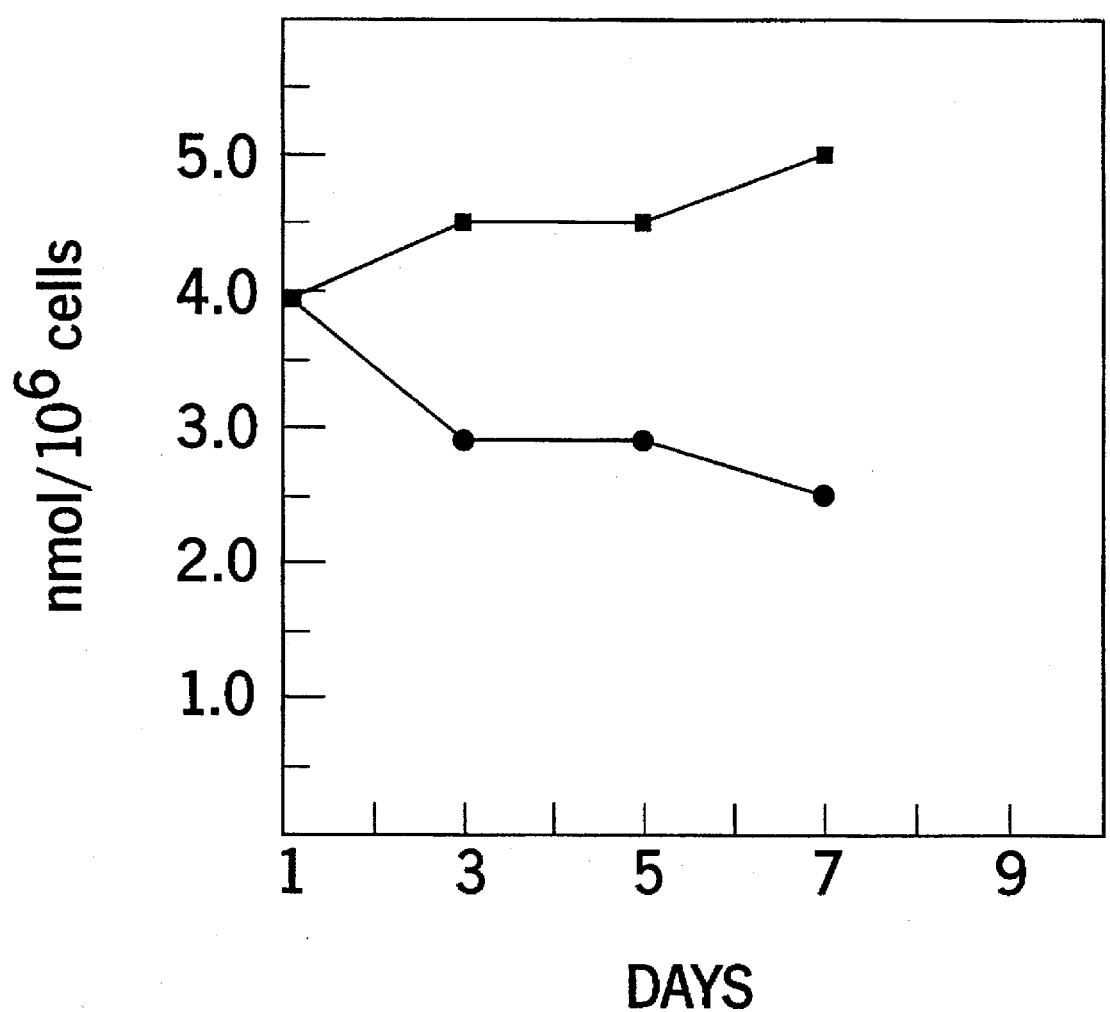
Figure 20C:
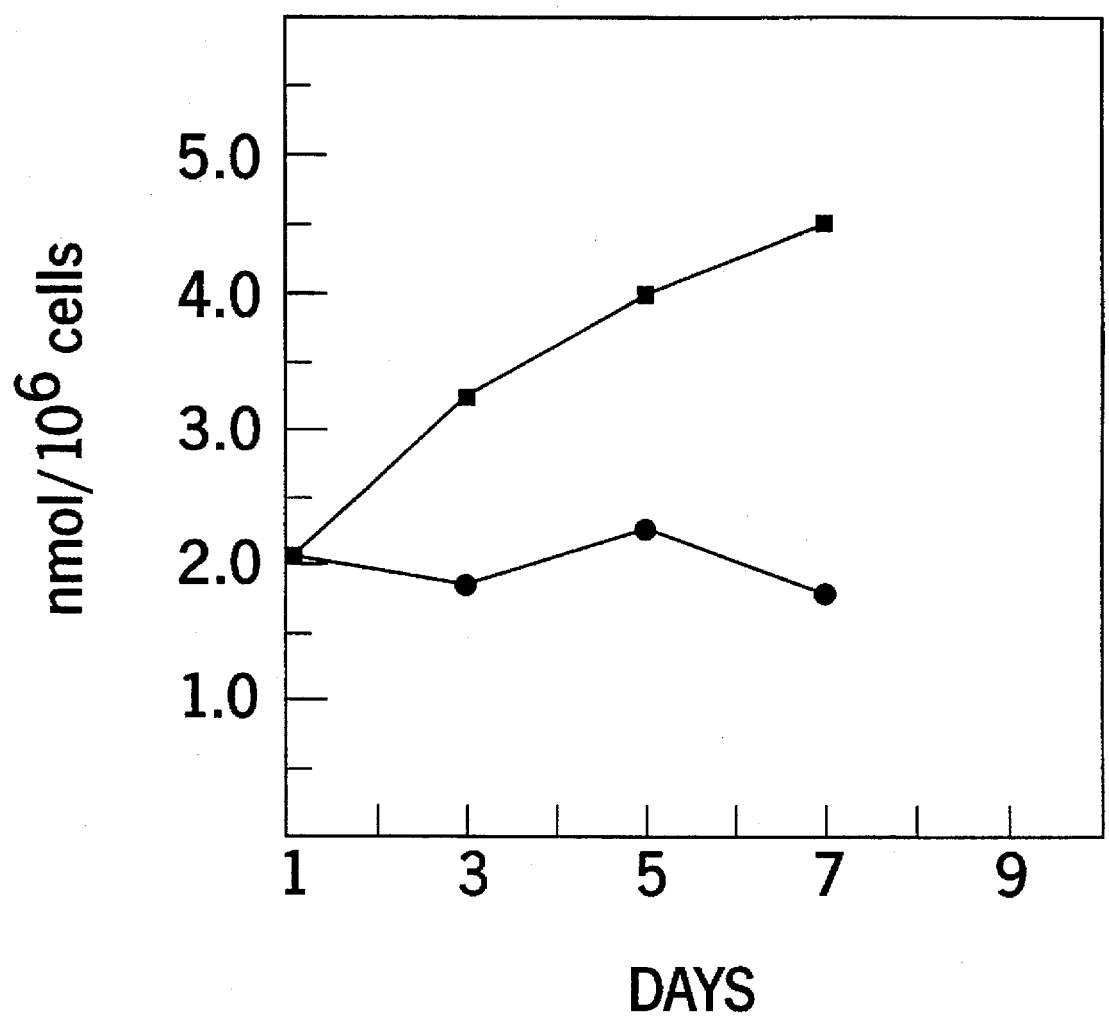

In the same manner as the hepatoma cell lines, these cells died out even when the endogenous pools of polyamines increased. See FIG. 20. However, a difference between the hepatoma cell line and the brain tumor cell line was that in the former, putrescine levels are increased, while in the latter, spermidine and spermine levels are increased. This is likely due to the presence of spermidine and spermine synthetases in the brain tumor cells which results in efficient aminopropylation of intracellular putrescine.

In Vivo Inhibitory Effect of DBP in Nude Mice Bearing Rat Cell Line and Human Cell Line-Derived Xenografts Nude mice aged four weeks were utilized. Rat hepatoma H-4-II-E ($10 \times 10^6$ cells), and human melanoma II-B-Mel-J ($5 \times 10^6$) were subcutaneously inoculated. Tumors developed between 15 to 24 days after inoculation. Toxicity of DBP was assayed in controls by adding 0.15% DBP to the drinking water over a period of 10 weeks. No toxic effects were detected. Pathological examination did not reveal any damage whatsoever to either the kidney or liver after 10 weeks. DBP was then administered orally to a group of 20 grafted mice, while a control group of 20 mice was left untreated. The progression of the rat hepatoma xenografts is shown in Table 2.

TABLE 2

| Tumor Volumes (cm³) in Nude Mice with Hepatoma Xenografts Treated with DBP | | | |
|---|---|---|---|
| Day | Controls | Treated | R control/treated |
| 0 | 0.8 | 0.84 | 0.95 |
| 5 | 1.92 | 0.80 | 2.40 |
| 10 | 4.30 | 1.12 | 3.86 |
| 15 | 5.79 | 1.99 | 5.17 |
| 20 | 11.04 | 1.73 | 6.39 |

After Day 20, the control mice died. The experimental mice were sacrificed, and pathological analyses revealed that:

1) DBP caused no damage to the internal organs. The kidneys of the treated animals were not affected by DBP treatment.
2) The control mice had developed lung tumors which were absent in the treated animals.
3) The hepatoma tumors themselves showed similar morphology in both the treated and untreated mice: differentiated cells, areas of necrosis, hemorrhages, and no mitosis.

When the same experiment was repeated on nude mice using human melanoma xenografts, the results were similar to those described immediately above. The results are tabulated in Table 3.

TABLE 3

Tumor Volumes (cm$^3$) in Nude Mice with Human Melanoma Xenografts Treated with DBP

| Day | Controls | Treated | R control/treated |
|-----|----------|---------|-------------------|
| 0   | 0.26     | 0.13    | 1.96              |
| 10  | 6.20     | 2.45    | 2.53              |
| 20  | 8.10     | 2.51    | 3.23              |
| 30  | 12.40    | 2.49    | 4.98              |
| 40  | 16.80    | 2.50    | 6.72              |

In the same fashion as in the hepatoma xenografts, treatment with DBP strongly decreased the size of the tumors. The mice died after Day 40.

Pathological analyses showed that the melanoma tumors had different morphology between the treated and untreated animals. The controls showed intense mitotic activity in the tumors, while in the treated mice the tumors showed large areas of necrosis and very low mitotic activity.

Analysis of the polyamine levels in the melanoma tissues of both the treated and untreated mice did not reveal any significant difference between the two.

Discussion

Based upon the above experiments, the following conclusions can be drawn in regard to N,N'-dibenzyldiaminoalkanes:

N,N'-dibenzylputrescine (DBP) and N,N'-dibenzylcadaverine (DBC) inhibit proliferation of rat liver hepatoma cells, human melanoma cells, and human brain tumor cells when assayed in vitro. However, this in vitro inhibition does not appear to be linked to the depletion of intracellular polyamine pools.

DBP is a poor inhibitor of ODC when assayed in vitro, but does exhibit ODC inhibition when added to cell cultures.

DBP is a competitive inhibitor of putrescine uptake by cells. In the hepatoma cell line, the $K_m$ for active putrescine transport into the cell is similar to the $K_i$ determined for DBP. Therefore, both putrescine and DBP appear to share similar affinities for the transport system. However, even in the presence of a tenfold excess of putrescine, DBP still exerts its inhibitory effect. This suggests that the two compounds may not share the same transport mechanism.

DBP compares favorably in action with DFMO, a well-known inhibitor of cell proliferation which functions by depleting intracellular polyamine levels. To its credit, though, in the rat hepatoma cell line, DBP exerts a cytostatic effect at a concentration of only 100 μM, while DFMO requires a tenfold increase in concentration of 1 mM to achieve similar results. DBP is also less toxic in vivo than DFMO. At a concentration of 0.15%, DBP inhibited cell-derived xenografts in nude mice without any signs of toxicity to the mice. DFMO requires a tenfold higher concentration (2%) to produce the same effect.

Perhaps most important of the findings is that DBP clearly reduces the volumes of tumors in cell-derived xenografts. In nude mice, DBP reduced the size of cell-derived xenografts by a factor of 6 to 7 when added to drinking water at non-toxic levels. As noted above, the N,N'-dibenzyldiaminoalkanes therefore find use as enhancers of radiotherapeutic regimes, where decrease in tumor size is often crucial for the success of conjunctive therapies, such as ionizing radiation treatment.

A further advantage of N,N'-dibenzylaminoalkanes, and one that should not be overlooked, is that they are exceedingly simple to manufacture in large-scale syntheses. This is not a trivial fact because, like DFMO, N,N'-dibenzyldiaminoalkanes are administered in relatively large doses. DFMO, with its difluoromethyl moiety does not share this important quality.

It is understood that the present invention is not limited to the above-described embodiments, but encompasses all such embodiments encompassed by the following claims.

What is claimed is:

1. A method of inhibiting growth of cancer cells which are sensitive to one or more of the following compounds, the method comprising contacting the cells with an effective growth inhibiting amount of a compound selected from the group consisting of linear $C_2$–$C_{10}$ N,N'-dibenzyl α,ω-diaminoalkanes, branched $C_2$–$C_{10}$ N,N'-dibenzyl α,ω-diaminoalkanes, pharmaceutically-suitable salts thereof and mixtures thereof.

2. The method according to claim 1, wherein an amount of said compound which is effective to inhibit growth of cancer cells is administered to a human cancer patient in need thereof.

3. The method according to claim 2, wherein said amount of said compound is administered orally in combination with a pharmaceutically-acceptable carrier.

4. The method according to claim 2, wherein said amount of said compound is administered parenterally in combination with a pharmaceutically-acceptable carrier.

5. The method according to claim 2, wherein said amount of said compound is administered via an administration means selected from the group consisting of intravenous administration, intraarterial administration, intratumor administration, intramuscular administration, intraperitoneal administration, and subcutaneous administration; in combination with a pharmaceutically-acceptable carrier.

6. A method of inhibiting growth of cancer cells which are sensitive to one or more of the following comounds, the method comprising contacting the cells with an effective growth-inhibiting amount of a compound selected from the group consisting of

wherein X is an integer of from 3–8, pharmaceutically-suitable salts thereof, and mixtures thereof.

7. The method according to claim 6, wherein an amount of said compound which is effective to inhibit growth of cancer cells is administered to a human cancer patient in need thereof.

8. The method according to claim 7, wherein said amount of said compound is administered orally in combination with a pharmaceutically-acceptable carrier.

9. The method according to claim 7, wherein said amount of said compound is administered parenterally in combination with a pharmaceutically-acceptable carrier.

10. The method according to claim 7, wherein said amount of said compound is administered via an administration means selected from the group consisting of intravenous administration, intraarterial administration, intratumor administration, intramuscular administration, intraperitoneal administration, and subcutaneous administration; in combination with a pharmaceutically-acceptable carrier.

11. The method according to claim 6, wherein an amount of N,N'-dibenzylputrescine which is effective to inhibit growth of cancer cells is administered to a human cancer patient in need thereof.

12. The method according to claim 11, wherein said amount of N,N'-dibenzylputrescine is administered orally in combination with a pharmaceutically-acceptable carrier.

13. The method according to claim 11, wherein said amount of N,N'-dibenzylputrescine is administered parenterally in combination with a pharmaceutically-acceptable carrier.

14. The method according to claim 11, wherein said amount of N,N'-dibenzylputrescine is administered via an administration means selected from the group consisting of intravenous administration, intraarterial administration, intratumor administration, intramuscular administration, intraperitoneal administration, and subcutaneous administration; in combination with a pharmaceutically-acceptable carrier.

15. The method according to claim 6, wherein an amount of N,N'-dibenzylcadaverine which is effective to inhibit growth of cancer cells is administered to a human cancer patient in need thereof.

16. The method according to claim 15, wherein said amount of N,N'-dibenzylcadaverine is administered orally in combination with a pharmaceutically-acceptable carrier.

17. The method according to claim 15, wherein said amount of N,N'-dibenzylcadaverine is administered parenterally in combination with a pharmaceutically-acceptable carrier.

18. The method according to claim 15, wherein said amount of N,N'-dibenzylcadaverine is administered via an administration means selected from the group consisting of intravenous administration, intraarterial administration, intratumor administration, intramuscular administration, intraperitoneal administration, and subcutaneous administration in combination with a pharmaceutically-acceptable carrier.

* * * * *